United States Patent [19]

Shimada et al.

[11] Patent Number: 5,366,856
[45] Date of Patent: Nov. 22, 1994

[54] SILVER HALIDE COLOR PHOTOSENSITIVE MATERIALS

[75] Inventors: Yasuhiro Shimada; Hiroyuki Yoneyama, both of Kanagawa, Japan

[73] Assignee: Fuji Photo Film Co., Ltd., Kanagawa, Japan

[21] Appl. No.: 64,586

[22] Filed: May 21, 1993

[30] Foreign Application Priority Data

May 26, 1992 [JP] Japan .................................. 4-157332

[51] Int. Cl.$^5$ .................................................. G03C 7/38
[52] U.S. Cl. ..................................... 430/558; 430/384; 430/385
[58] Field of Search ................ 430/558, 543, 384, 385

[56] References Cited

FOREIGN PATENT DOCUMENTS

| | | | |
|---|---|---|---|
| 0456226 | 5/1991 | European Pat. Off. | G03C 7/38 |
| 0484909 | 11/1991 | European Pat. Off. | G03C 7/38 |
| 0488248 | 6/1992 | European Pat. Off. | |
| 0518238 | 12/1992 | European Pat. Off. | |

*Primary Examiner*—Lee C. Wright
*Attorney, Agent, or Firm*—Sughrue, Mion, Zinn, Macpeak & Seas

[57] ABSTRACT

A silver halide color photosensitive materials wherein a coupler represented by the formula indicated below is included in at least one layer on a support. In the formula, for example, Za represents —NH—, Zb represents —C($R_4$)= and Zc represents —N=. $R_1$, $R_2$ and $R_3$ each represents an electron withdrawing group of which the Hammett substituent group constant $\sigma_p$ value is 0.20 or above. However, the sum of the $\sigma_p$ values of $R_1$ and $R_2$ is 0.65 or above. $R_4$, $R_a$, $R_b$, $R_c$, $R_d$ and $R_e$ each represents a hydrogen atom or a substituent group. However, for example at least one of $R_a$, $R_b$, $R_c$, $R_d$ and $R_e$ represents an electron withdrawing group, and the sum of the Hammett substituent group constant $\sigma_p$ values of each of $R_a$, $R_b$, $R_c$, $R_d$ and $R_e$ is 0.5 or above.

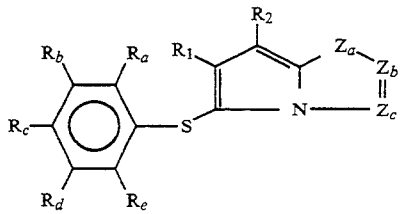

22 Claims, No Drawings

SILVER HALIDE COLOR PHOTOSENSITIVE MATERIALS

FIELD OF THE INVENTION

The present invention concerns silver halide color photographic photosensitive materials (referred to hereinafter simply as photosensitive materials) which contain novel couplers.

BACKGROUND OF THE INVENTION

The formation of color images by means of indophenol, indoaniline, indamine, azomethine, phenoxazine, phenazine and related dyes by reacting couplers with a primary aromatic amine-based color developing agent which has been oxidized by image-wise exposed silver halide as the oxidizing agent is well known. The subtractive color method is used in photographic systems of this type and the colored image is formed by means of yellow, magenta and cyan dyes.

From among these, phenol or naphthol-based couplers are generally used for forming a cyan dye image. However, these couplers give rise to serious problems in that color reproduction is greatly downgraded since they have undesirable absorption in the yellow and green regions.

The heterocyclic compounds disclosed for example in U.S. Pat. Nos. 4,728,598 and 4,873,183 and in EP 249,453A2 have been suggested as a means of resolving the above problem. However, these compounds have a low coupling activity and give rise to further difficulties in that the fastness to heat and light of the dyes which are formed is poor.

The pyrrolopyrazole couplers disclosed in European Patent laid open 0,456,226 have been proposed as couplers which overcome this problem. Although these couplers have good color forming properties and hue, they are still unsatisfactory. Moreover, the storage properties and the stability of the couplers in a photosensitive material under hot, dark conditions are poor.

Pyrroloimidazole couplers have also been proposed in European Patent laid open 0,484,909. The hue and color forming properties and the fastness of the colored image with these pyrroloimidazole couplers needs further investigation.

SUMMARY OF THE INVENTION

Hence, one object of the present invention is to provide photosensitive materials which provide excellent color reproduction properties.

Another object of the invention is to provide photosensitive materials which contain novel couplers having excellent stability in the photosensitive material, a high coupling activity, and excellent fastness of the formed dye image.

As a result of a thorough investigation of the above-mentioned pyrrolopyrazole couplers, the inventors have discovered that the objects of the present invention can be realized by means of a silver halide color photographic photosensitive material wherein at least one of coupler represented by formula (I) indicated below is included in at least one layer on a support.

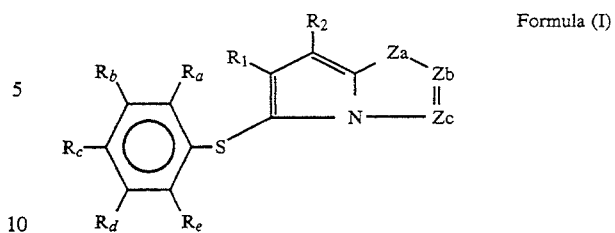

Formula (I)

In formula (I), Za represents —NH— or —CH($R_3$)—, and Zb and Zc each represents —C($R_4$)= or —N=. However, when Zb is —C($R_4$)=, Zc is not —C($R_4$)= at the same time as Za is —NH—, or Zc is not —N= at the same time as Za is —CH($R_3$)—. $R_1$, $R_2$ and $R_3$ each represents an electron withdrawing group having a Hammett substituent group constant $\sigma_p$ of 0.20 or above. However, the sum of the $\sigma_p$ values of $R_1$ and $R_2$ is 0.65 or above. $R_4$, $R_a$, $R_b$, $R_c$, $R_d$ and $R_e$ each represents a hydrogen atom or a substituent group. However, in a case where there are two $R_4$ groups in the formula, these may be the same or different. Furthermore, at least one of $R_a$, $R_b$, $R_c$, $R_d$ and $R_e$ represents an electron withdrawing group, and the sum of the respective Hammett substitution constant $\sigma_p$ values of $R_a$, $R_b$, $R_c$, $R_d$ and $R_e$ is 0.5 or above, or at least two of $R_a$, $R_b$, $R_c$, $R_d$ and $R_e$ are fluorine atoms and the sum of the respective Hammett substituent group constant $\sigma_p$ values of $R_a$, $R_b$, $R_c$, $R_d$ and $R_e$ is 0.15 or above.

DETAILED DESCRIPTION OF THE INVENTION

The compounds of the present invention are described in detail below.

In formula (I), Za represents —NH— or —CH($R_3$)—, and Zb and Zc each represents —C($R_4$)= or —N=. In a case where there are two $R_4$ groups in the formula these may be the same or different. However, when Zb is —C($R_4$)=, Zc is not —C($R_4$)— at the same time as Za is —NH— and Zc is not —N= at the same time as Za is —CH($R_3$)—.

The couplers of the present invention can be represented by the formulas (II) to (VII) shown below:

Formula (II)

Formula (III)

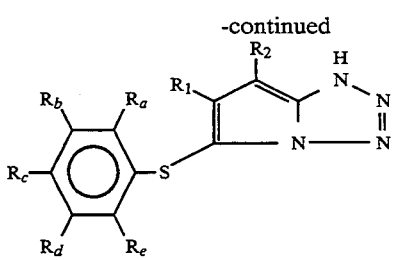

Formula (IV)

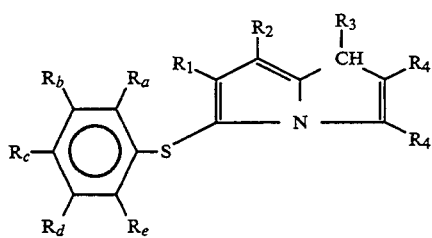

Formula (V)

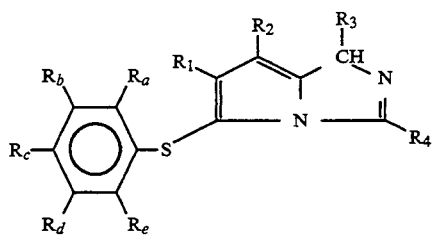

Formula (VI)

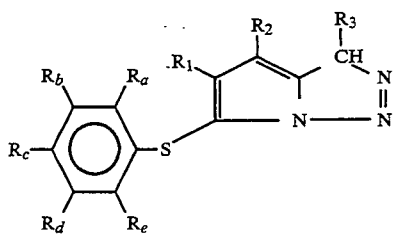

Formula (VII)

In these formulas, $R_1$, $R_2$, $R_3$, $R_4$, $R_a$, $R_b$, $R_c$, $R_d$ and $R_e$ each has the same meaning as in formula (I).

The couplers represented by formula (II) or (III) are preferred in the present invention, and the couplers represented by formula (II) are the most desirable.

In the couplers of the present invention, $R_1$, $R_2$ and $R_3$ are all electron withdrawing groups of which the Hammett substituent group constant $\sigma_p$ values are 0.20 or above for each, preferably 0.30 or above for each. They are preferably electron withdrawing groups of which the $\sigma_p$ value is not more than 1.0 for each as an upper limit. The sum of the $\sigma_p$ values of $R_1$ and $R_2$ is 0.65 or above, preferably 0.70 or above, with about 1.8 as an upper limit. The couplers of the present invention perform excellently as cyan couplers as a result of the introduction of these strong electron withdrawing groups.

Hammett's rule is an empirical rule introduced by L. P. Hammett in 1935 in order to discuss quantitatively the effects of substituent groups on the reactions and equilibria of benzene derivatives, and its appropriateness is now widely recognized. The substituent group constants recognized by Hammett's rule are the $\sigma_p$ value and the $\sigma_m$ value, and these values have been disclosed in general text books, and they have been given in detail for example in *Lange's Handbook of Chemistry*, 12th Edition, 1979, edited by J. A. Dean (McGraw-Hill) and in Kagaku no Ryoiki Zokan No.122, pages 96 to 103 1979 (Nanedo). In the present invention, $R_1$, $R_2$, $R_3$, $R_a$, $R_b$, $R_c$, $R_d$ and $R_e$ are specified according to the Hammett substituent group constant $\sigma_p$, but this does not that they are limited to the substituent groups having known literature values disclosed in these books. Substituent groups are of course included even if the $\sigma_p$ value is unknown provided that the value when it is measured in accordance with Hammett's rule is within range disclosed above.

Acyl groups, acyloxy groups, carbamoyl groups, alkoxycarbonyl groups, aryloxycarbonyl groups, cyano group, nitro group, dialkylphosphono groups, diarylphosphono groups, diarylphosphinyl groups, alkylsulfinyl groups, arylsulfinyl groups, alkylsulfonyl groups, arylsulfonyl groups, sulfonyloxy groups, acylthio groups, sulfamoyl groups, thiocyanato group, thiocarbonyl groups, alkyl groups which are substituted with at least two halogen atoms, alkoxy groups which are substituted with at least two halogen atoms, aryloxy groups which are substituted with at least two halogen atoms, alkylamino groups which are substituted with at least two halogen atoms, alkylthio groups which are substituted with at least two halogen atoms, aryl groups which are substituted with other electron withdrawing groups having a $\sigma_p$ of 0.20 or above, heterocyclic groups, chlorine atom, bromine atom, azo groups, and selenocyanato group are actual examples of $R_1$, $R_2$ and $R_3$ which are electron withdrawing groups having an $\sigma_p$ value of 0.20 or above. The groups which can be substituted by the above substituent groups, may be further substituted with additional substituent groups such as those representative of $R_4$ which are described hereinafter.

$R_1$, $R_2$ and $R_3$ are described in more detail below. Thus, acyl groups (for example acetyl, 3-phenylpropionyl, benzoyl, 4-dodecyloxybenzoyl), acyloxy groups (for example acetoxy), carbamoyl groups (for example, carbamoyl, N-ethylcarbamoyl, N-phenylcarbamoyl, N, N-dibutylcarbamoyl, N-(2-dodecyloxyethyl) carbamoyl, N-(4-n-pentadecanamido)phenyl-carbamoyl, N-methyl-N-dodecylcarbamoyl, N-{3-(2,4-di-tert-amyl-phenoxy)propyl}carbamoyl), alkoxycarbonyl groups (for example methoxycarbonyl, ethoxycarbonyl, isopropyloxy-carbonyl, tertbutyloxycarbonyl, iso-butyloxycarbonyl, butyloxycarbonyl, dodecyloxycarbonyl, octadecyloxycarbonyl), aryloxycarbonyl groups (for example phenoxycarbonyl), cyano group, nitro group, dialkylphosphono groups (for example dimethylphosphono), diarylphosphono groups (for example diphenylphosphono), diarylphosphinyl groups (for example diphenylphosphinyl), alkylsulfinyl groups (for example 3-phenoxypropylsulfinyl), arylsulfinyl groups (for example) 3-pentadecylphenylsulfinyl), alkylsulfonyl groups (for example methanesulfonyl, octanesulfonyl), arylsulfonyl groups (for example benzenesulfonyl, toluenesulfonyl), sulfonyloxy groups (for example methanesulfonyloxy, toluenesulfonyloxy), acylthio groups (for example acetylthio, benzoylthio), sulfamoyl groups (for example N-ethylsulfamoyl, N,N-dipropylsulfamoyl, N-(2-dodecyloxyethyl)sulfamoyl, N-ethyl-N-dodecylsulfamoyl, N,N-diethylsulfamoyl), thiocyanato group, thiocarbonyl groups (for example, methylthiocarbonyl, phenylthiocarbonyl), alkyl groups substituted which are substituted with at least two halogen atoms (for example, trifluoromethyl, heptafuluoropropyl), alkoxy groups which are substituted with least two halogen atoms (for example trifluoromethyloxy), aryloxy groups which are substituted with at least two halogen atoms (for example pentafluorophenyloxy), alkylamino groups which are substituted with at least two halogen atoms (for example N,N-di-(trifluoromethyl)amino), alkylthio groups which are substituted with at least two halogen atoms (for example difluoromethylthio, 1,1,2,2-tetrafluoroethylthio), aryl groups which are substituted with at least two other electron withdrawing groups of which the $\sigma_p$ value is 0.20 or above (for example 2,4-dinitrophenyl, 2,4,6-trichlorophenyl, pentachlorophenyl), heterocyclic groups ( for example 2-benzoxazolyl, 2-benzothiazolyl, 1-phenyl-2-benzimidazolyl, 5-chloro-1-tetrazolyl, 1-pyrrolyl), chlorine atom, bromine atom, azo groups ( for example phenylazo ) or selenocyanato groups are all representative of electron withdrawing groups of which the $\sigma_p$ value is 0.20 or above.

Acyl groups, acyloxy groups, carbamoyl groups, alkoxycarbonyl groups, aryloxycarbonyl groups, cyano group, nitro group, alkylsulfinyl groups, arylsulfinyl groups, alkylsulfonyl groups, arylsulfonyl groups, sulfamoyl groups, alkyl groups which are substituted with two or more halogen atoms, alkylthio groups which are substituted with two or more halogen atoms, aryloxy groups which are substituted with two or more halogen atoms, aryl groups which are substituted with two or more halogen atoms, aryl groups which are substituted with two or more nitro groups, and heterocyclic groups, can be cited as preferred groups for $R_1$, $R_2$ and $R_3$. Acyl groups, alkoxycarbonyl groups, nitro group, cyano group, arylsulfonyl groups, carbamoyl groups and alkyl groups which are substituted with two or more halogen atoms are more desirable, and cyano groups, alkoxycarbonyl groups and aryloxycarbonyl groups are even more desirable. From among these groups, the cyano group is the most desirable for $R_1$ and $R_3$ and branched chain alkoxycarbonyl groups are the most desirable for $R_2$.

The $\sigma_p$ values of typical electron withdrawing groups of which the up value is 0.2 or above are for example, bromine atom (0.23), chlorine atom ( 0.23 ), cyano group (0.66 ), nitro group (0.78 ), trifluoromethyl group (0.54), tribromomethyl group (0.29 ), trichloromethyl group (0.33), carboxyl group (0.45), acetyl group (0.50), benzoyl group (0.43), acetyloxy group (0.31), trifluoromethanesulfonyl group (0.92), methanesolfonyl group (0.72), benzenesulfonyl group (0.70), methanesulfinyl group (0.49 ), carbamoyl group (0.36) methoxycarbonyl group (0.45), ethoxycarbonyl group, (0.45), pyrazolyl group (0.37 ), methanesulfonyloxy group (0.36), dimethoxyphosphoryl group (0.60 ), sulfamoyl group (0.57).

$R_4$, $R_a$, $R_b$, $R_c$ $R_d$ and $R_e$ each represents a hydrogen atom or a substituent group (including atoms). Halogen atoms, alkyl groups, aryl groups, heterocyclic groups, cyano group, hydroxy group, nitro group, carboxy group, sulfo group, amino group, alkoxy groups, aryloxy groups, acylamino groups, alkylamino groups, anilino group, ureido groups, sulfamoylamino groups, alkylthio groups, arylthio groups, alkoxycarbonylamino groups, sulfonamido groups, carbamoyl groups, sulfamoyl groups, sulfonyl groups, alkoxycarbonyl groups, heterocyclic oxy groups, azo groups, acyloxy groups, carbamoyloxy groups, silyloxy groups, aryloxycarbonylamino groups, imido groups, heterocyclic thio groups, sulfinyl groups, phosphonyl groups, aryloxycarbonyl groups, acyl groups and azolyl groups, for example, can be cited as substituent groups. These groups may be further substituted with substituent groups as indicated for $R_4$.

More Particularly, $R_4$, $R_a$, $R_b$, $R_c$, $R_d$ and $R_e$ each represents a hydrogen atom, a halogen atom (for example chlorine, bromine), an alkyl group (for example linear chain or branched chain alkyl, aralkyl, alkenyl, alkynyl, cycloalkyl or cycloalkenyl group of a carbon number 1 to 32, actual examples including methyl, ethyl, propyl, isopropyl, tert-butyl, dodecyl, tert-amyl, tertoctyl, 2-methanesulfonylethyl, 3-(3-pentadecylphenoxy)propyl, 3-{4-{2-[4-(4-hydroxyphenylsulfonyl)-phenoxy]dodecanamido}phenyl}propyl, 2-ethoxytridecyl, trifluoromethyl, cyclopentyl, 3-(2,4-di-tert-amylphenoxy)propyl), an aryl group (for example phenyl, 4-tert-butylphenyl, 2,4-di-tert-amylphenyl, 4-tetradecanamido phenyl), a heterocyclic group (for example 2-furyl, 2-thienyl, 2-pyrimidinyl, 2-benzothiazolyl), a cyano group, a hydroxy group, a nitro group, a carboxy group, an amino group, an alkoxy group (for example methoxy, ethoxy, butoxy, 2-methoxyethoxy, 2-dodecylethoxy, 2-methanesulfonylethoxy), an aryloxy group (for example phenoxy, 2methylphenoxy, 4-tert-butylphenoxy, 3-nitrophenoxy, 3-tert-butylcarbamoylphenoxy, 3-methoxycarbamoyl phenoxy), an acylamino group (for example acetamido, benzamido, tetradecanamido, 2-(2,4-di-tert-amylphenoxy)butanamido, 4-(3-tert-butyl-4-hydroxyphenoxy)butanamido, 2-{4-(4hydroxyphenylsulfonyl)phenoxy}decanamido), an alkylamino group (for example methylamino, butylamino, dodecylamino, diethylamino, methylbutylamino), an anilino group (for example phenylamino, 2-chloroanilino, 2-chloro-5tetradecanaminoanilino, 2-chloro-5-dodecyloxy-carbonylanilino, N-acetylanilino, 2-chloro-5-{2-(3-tert-butyl-4-hydroxyphenoxy)dodecanamido}anilino), a ureido group (for example phenylureido, methylureido, N,N-dibutylureido), a sulfamoylamino group (for example N,N-dipropylsulfamoylamino, N-methyl-N-decylsulfamoylamino), an alkylthio group (for example methylthio, octylthio, tetradecylthio, 2-phenoxyethylthio, 3-phenoxypropylthio, 3-(4-tert-butylphenoxy)propylthio), an arylthio group (for example phenylthio, 2-butoxy-5-tert-octylphenylthio, 3-pentadecylphenylthio, 2-carboxyphenylthio, 4tetradecanamidophenylthio), an alkoxycarbonylamino group (for example methoxycarbonylamino, tetradecyloxycarbonylamino), a sulfonamido group (for example, methanesulfonamido, butanesulfonamido, octanesulfonamido, hexadecanesulfonamido, benzenesulfonamido, p-toluenesulfonamido, octadecanesulfonamido, 2-methyloxy-5-tertbutylbenzenesulfonamido), a carbamoyl group (for example N-ethylcarbamoyl, N,N-dibutylcarbamoyl, N-(2-dodecyloxyethyl)carbamoyl, N-methyl-N-dodecylcarbamoyl, N-{3-(2,4- di-tert-amylphenoxy)propyl}carbamoyl), a sulfamoyl group (for example N-ethylsulfamoyl, N,N-dipropylsulfamoyl, N-(2-dodecyloxyethyl)sulfamoyl, N-ethyl-N-dodecylsulfamoyl, N,N-diethylsulfamoyl), a sulfonyl group (for example methanesulfonyl, octanesulfonyl, benzenesulfonyl, toluenesulfonyl), an alkoxycarbonyl group (for example methoxycarbonyl, butyloxycarbonyl, dodecyloxycarbonyl, octadecyloxycarbonyl), a heterocyclic oxy group (for example 1-phenyltetrazol-5-oxy, 2-tetrahydropyranyloxy), an azo group (for example phenylazo, 4-methoxyphenylazo, 4-pivaloylaminophenylazo, 2-hydroxy-4-propanoylphenylazo), an acyloxy group (for example acetoxy), a carbamoyloxy group (for example N-methylcarbamoyloxy, N-phenylcarbamoyloxy), a silyloxy group (for example trimethylsilyloxy, dibutylmethylsilyloxy), an aryloxycarbonylamino group (for example phenoxycarbonylamino), an imido group (for example, N-succinimido, N-phthalimido, 3-octadecenylsuccinimido), a heterocyclic thio group (for example 2-benzothiazolylthio, 2,4-diphenoxy-1,3,5-triazol-6-thio, 2-pyridylthio), a sulfinyl group (for example dodecanesulfinyl, 3-pentadecylphenylsulfinyl, 3-phenoxypropylsulfinyl), a phosphonyl group (for example phenoxyphosphonyl, octyloxyphosphonyl, phenylphosphonyl), an aryloxycarbonyl group (for example, phenoxycarbonyl), an acyl group (for example acetyl, 3-phenylpropanoyl, benzoyl, 4-dodecyloxybenzoyl) or an azolyl group (for example imidazolyl, pyrazolyl, 3-chloropyrazol-1-yl).

Alkyl groups, aryl groups, heterocyclic groups, cyano group, nitro group, acylamino groups, anilino groups, ureido groups, sulfamoylamino groups, alkylthio groups, arylthio groups, alkoxycarbonylamino groups, sulfonamido groups, carbamoyl groups, sulfamoyl groups, sulfonyl groups, alkoxycarbonyl groups, heterocyclic oxy groups, acyloxy groups, carbamoyloxy groups, aryloxycarbonylamino groups, imido groups, heterocyclic thio groups, sulfinyl groups, phosphonyl groups, aryloxycarbonyl groups, acyl groups and azolyl groups can be cited as preferred groups for $R_4$.

Alkyl groups and aryl groups are more desirable for $R_4$. Alkyl group or aryl groups which have at least one halogen atom, alkoxy groups, sulfonyl groups, sulfamoyl groups, carbamoyl groups, acylamido groups or sulfonamido groups as substituent groups are even more desirable. Alkyl groups or aryl groups which have at least one halogen atom, acylamido groups or sulfonamido groups are especially desirable as substituent groups representative of $R_4$, $R_a$, $R_b$, $R_c$, $R_d$ and $R_e$.

$R_a$, $R_b$, $R_c$, $R_d$ and $R_e$ represent hydrogen atoms or substituent groups, as described above, but (1) at least one of $R_a$ to $R_e$ represents an electron withdrawing group and the sum of the respective Hammett substituent group constant $\sigma_p$ values for $R_a$ to $R_e$ is 0.5 or above, and/or (2) at least two of $R_a$ to $R_e$ are fluorine atoms and the sum of the respective Hammett substituent group constant $\sigma_p$ values of $R_a$ to $R_e$ is 0.15 or above. Case (1) is preferred in the present invention.

In case (1), the sum of the $\sigma_p$ values of $R_a$ to $R_e$ when at least one of $R_a$ to $R_e$ represents an electron withdrawing group is preferably 0.8 or above and not more than 2.0, and it is most desirably 1.0 or above and not more than 2.0.

In case (1), in terms of the number of electron withdrawing groups, preferably at least two of $R_a$ to $R_e$ are electron withdrawing groups. In terms of the substitution position, at least one of $R_a$ and $R_e$ is preferably an electron withdrawing group, and most desirably, both $R_a$ and $R_e$ are electron withdrawing groups.

The electron withdrawing groups for $R_a$ to $R_e$ in case (1) should each have a $\sigma_p$ value greater than 0.0 (for example fluorine atom ($\sigma_p$ value 0.06)), and preferably they are electron withdrawing groups of which the $\sigma_p$ value is 0.2 or above as described earlier for $R_1$, $R_2$ and $R_3$. Preferred examples include bromine atom, chlorine atom, carbamoyl groups, alkoxycarbonyl groups, aryloxycarbonyl groups, cyano group, nitro group, alkyl-sulfinyl groups, arylsulfinyl groups, alkylsulfonyl groups, arylsulfonyl groups, sulfonyloxy groups, sulfamoyl groups and haloalkyl groups.

When, in case (2), at least two of $R_a$ to $R_e$ are fluorine atoms (and preferably at least three of these groups, and most desirably all of these groups, are fluorine atoms), the sum of the $\sigma_p$ values of $R_a$ to $R_e$ is preferably 0.2 or above and not more than 2.0, and most desirably it is 0.28 or above and not more than 2.0.

Preferred examples of the groups $R_a$ to $R_e$ which are not electron withdrawing groups in cases (1) and (2) include hydrogen atom, alkyl groups, alkoxy groups, acylamino groups and sulfonamido groups.

The sum of the respective Hammett substituent group constant $\sigma_p$ values of $R_a$ to $R_e$ is 0.5 or above and some typical combinations are indicated below, but the invention is not limited to these examples:

| $R_a$ | $R_b$ | $R_c$ | $R_d$ | $R_e$ | Total |
|---|---|---|---|---|---|
| H | H | H | H | CN | 0.66 |
| H | H | H | H | NO$_2$ | 0.78 |
| H | H | NO$_2$ | H | NO$_2$ | 1.56 |
| CN | H | H | H | CN | 1.32 |
| CN | CH$_3$ | H | H | CN | 1.16 |
| CF$_3$ | H | H | H | H | 0.54 |
| CO$_2$CH$_3$ | H | H | H | Br | 0.68 |
| Br | H | NHCOCH$_3$ | H | CN | 0.89 |
| Br | H | Br | H | CONH$_2$ | 0.82 |
| COCH$_3$ | H | COCH$_3$ | H | COCH$_3$ | 1.50 |
| Cl | Cl | Cl | Cl | Cl | 1.15 |
| Br | Br | Br | B | Br | 1.15 |
| Br | H | Br | H | Br | 0.69 |
| COOH | H | COCH$_3$ | H | Br | 1.18 |
| Cl | H | SO$_2$CH$_3$ | H | Cl | 1.18 |
| Br | H | SO$_2$CH$_3$ | H | Br | 1.18 |
| COOH | H | NO$_2$ | H | Br | 1.45 |
| Cl | Cl | CO$_2$CH$_3$ | Cl | Cl | 1.37 |
| Br | H | Br | H | CO$_2$CH$_3$ | 0.91 |
| Br | H | CO$_2$CH$_3$ | H | CN | 1.34 |
| F | H | F | H | F | 0.18 |
| F | F | F | F | F | 0.30 |

With the couplers represented by formula (I), the groups $R_1$, $R_2$, $R_3$ and $R_4$ sometimes contain coupler residual groups which can be represented by formula (I) and form dimers or larger oligomers. Also the $R_1$, $R_2$, $R_3$ or $R_4$ groups may contain macromolecular chains and form homopolymers or copolymers. The homopolymers or copolymers which contain macromolecular chains are typically homopolymers or copolymers of addition polymerizable ethylenic-type unsaturated compounds which have a coupler residual group which can be represented by general formula (I). In this case, one or more cyan coupler forming repeating unit, which has a coupler residual group which can be represented by general formula (I), may be included in the polymer, or it may be a copolymer which contains one or more than one type of non-color forming ethylenic-type monomer which does not undergo coupling with the oxidation products of a primary aromatic amine developing agent such as an acrylic acid ester, a methacrylic acid ester or a maleic acid ester as a copolymer component.

Actual examples of couplers of the present invention are indicated below, but the invention is not limited to the examples:

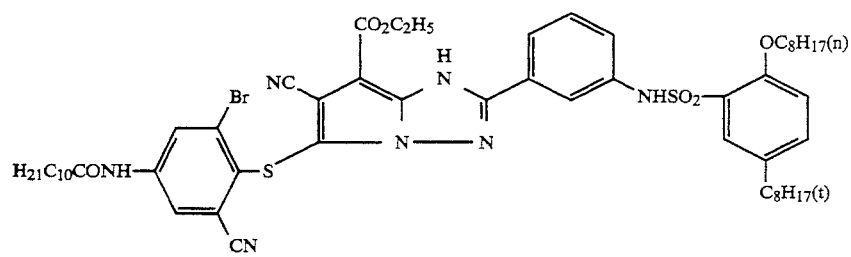
1)
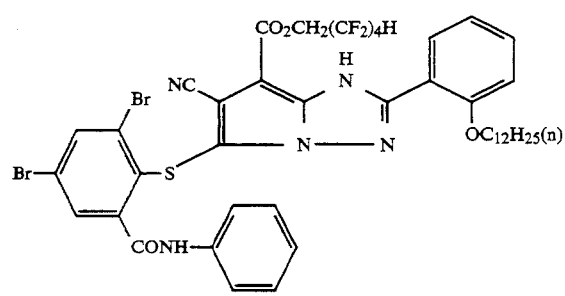
2)
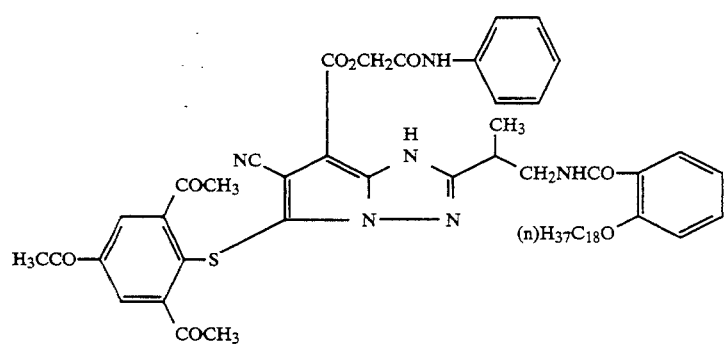
3)
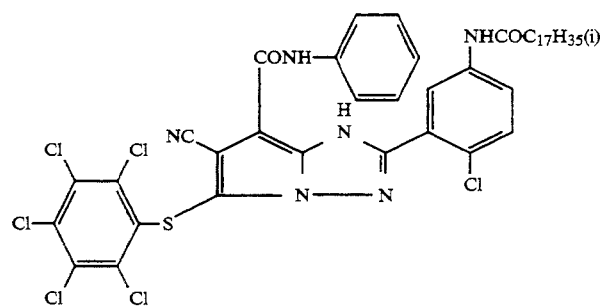
4)
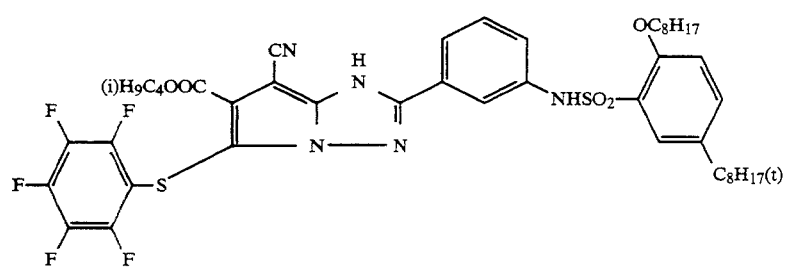
5)

6)
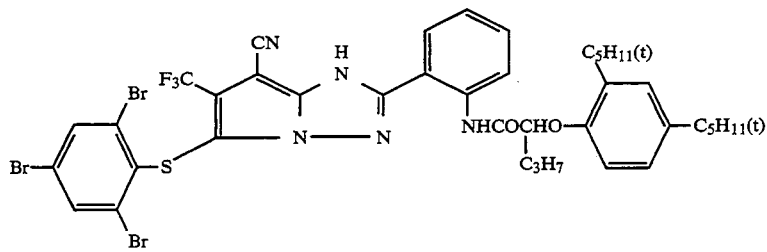
7)
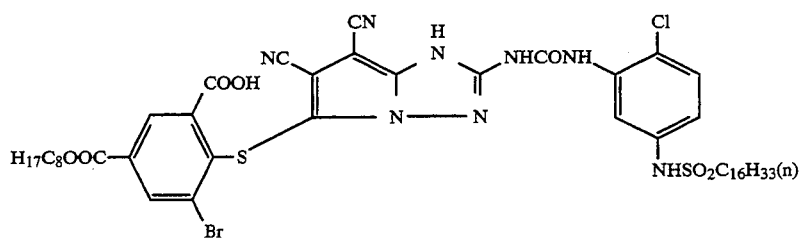
8)
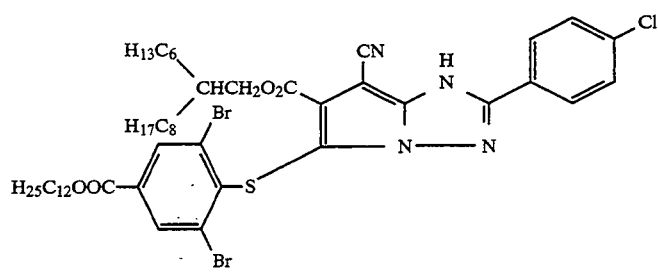
9)
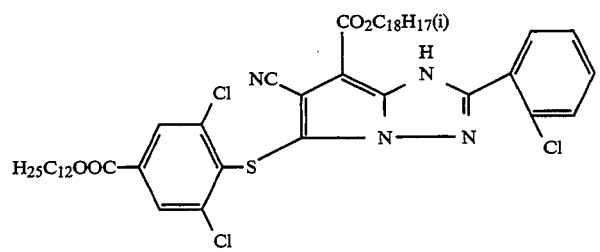
10)
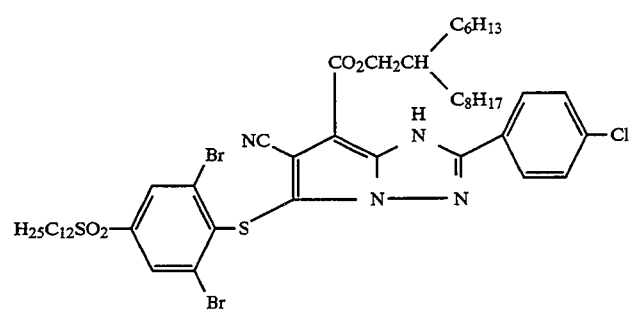
11)
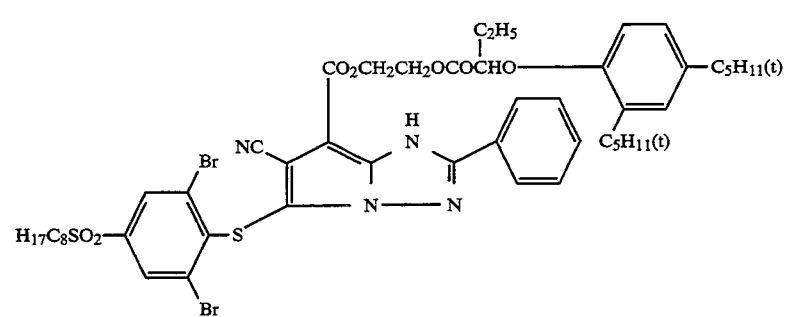

-continued
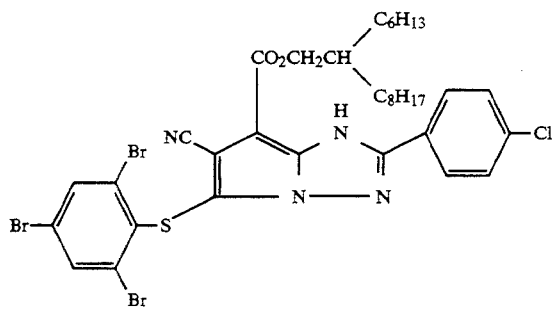
12)
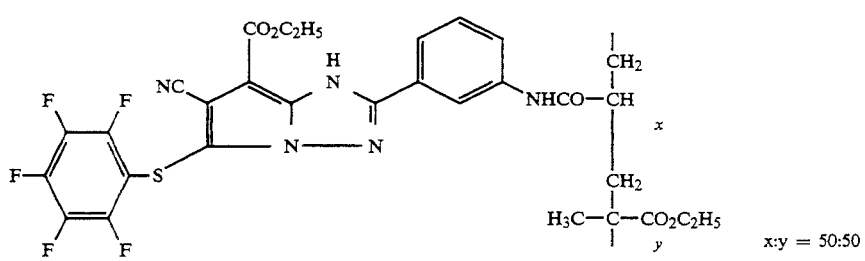
13)
x:y = 50:50
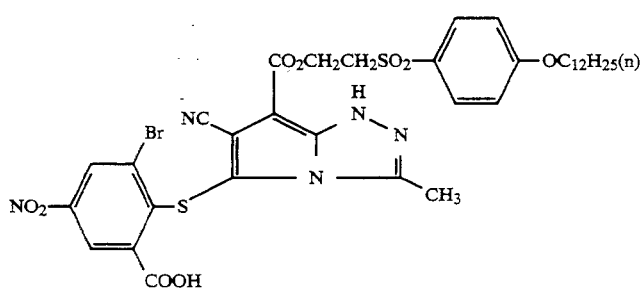
14)
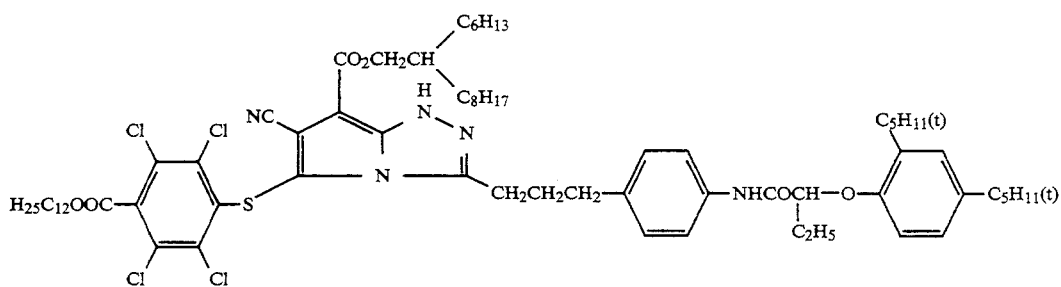
15)
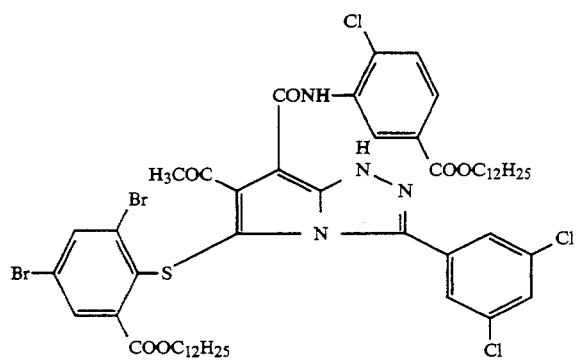
16)

-continued
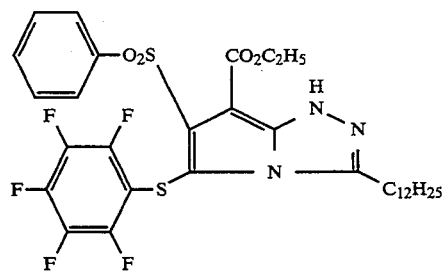
17)
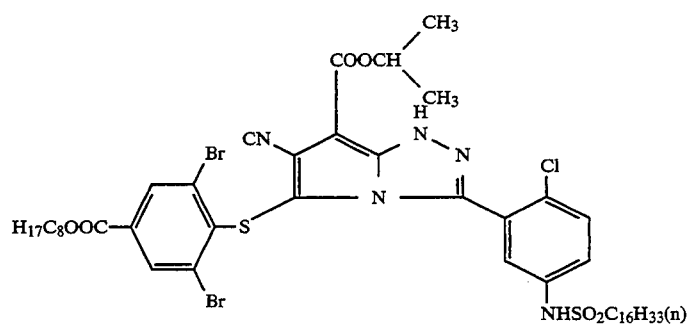
18)
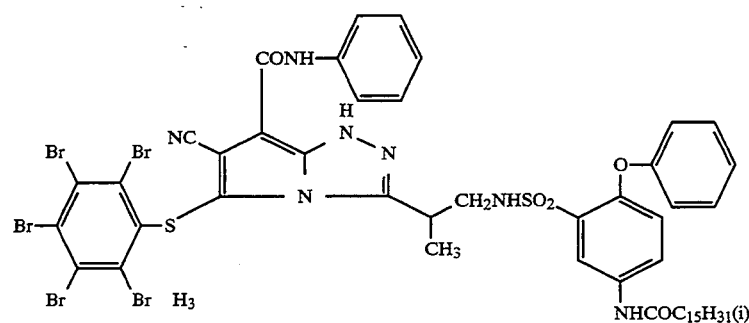
19)
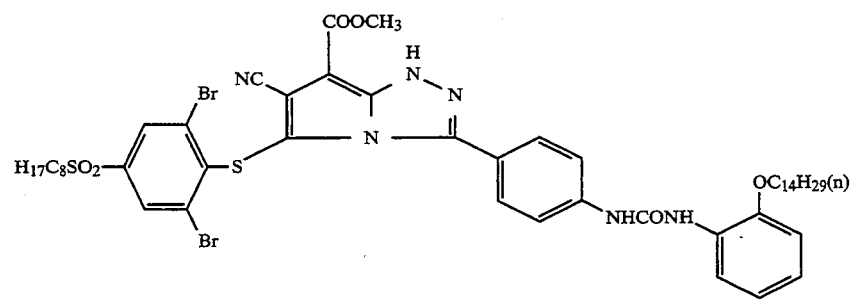
20)
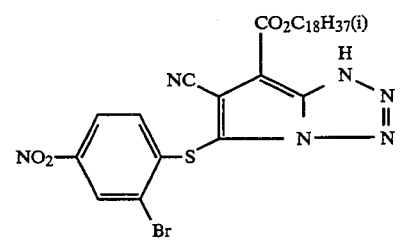
21)

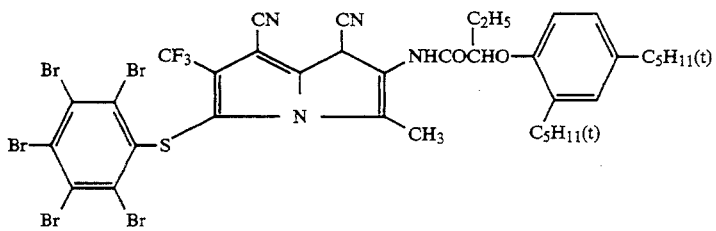

22)

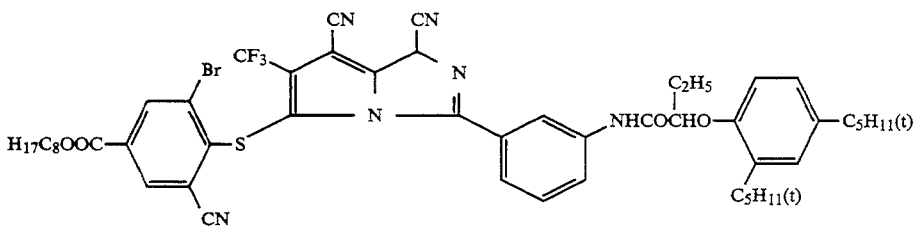

23)

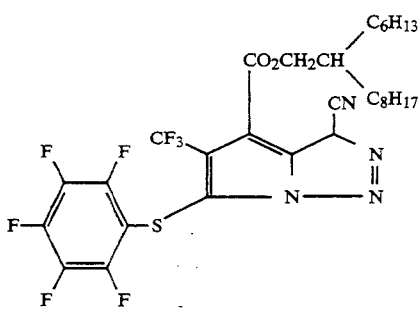

24)

Intermediates of the compounds of the present invention can be prepared using known methods. They can be prepared using the methods disclosed in *J. Chem. Soc.* page 5149 (1962), *J. Am. Chem. Soc.* No. 81, page 2452 (1959) and *Heterocyclic*, No.27, page 2301 (1988) and *IZV. Akad. Nauk SSSR, Ser. Khim.* page 582 (1970) for example, and the methods in the literature cited in these references or analogous methods. Reference can also be made to the abovementioned disclosures in connection with the starting materials and intermediates for these preparations.

Actual examples of synthesis are described below.

Example of Synthesis 1 The Preparation of Illustrative

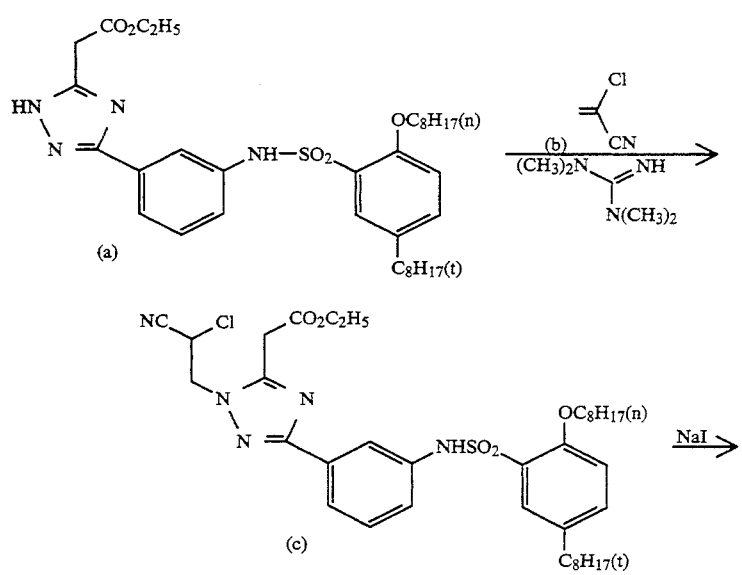

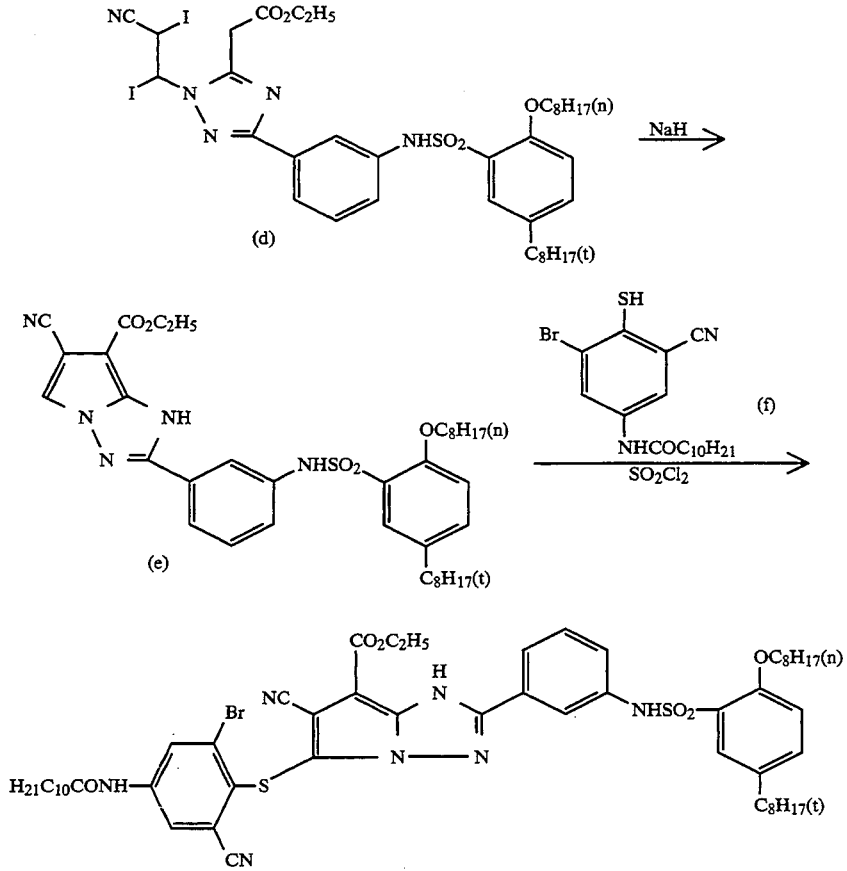

1,1,3,3-tetramethylguanidine (3.45 grams, 0.03 mol) was added dropwise at room temperature over a period of 15 minutes to a 300 ml solution of a tetrahydrofuran compound a (62.6 grams, 0.10 mol) and α-chloroacrylonitrile compound b (11.3 grams, 0.13 mol) and the mixture was stirred for 8 hours. Water was added and the mixture was extracted three times with ethyl acetate (500 ml). The organic layer was washed with water and saturated salt water and then dried over anhydrous sodium sulfate. The solvent was distilled off under reduced pressure. The product was refined using silica gel column chromatography and compound c was obtained (42.8 grams, 60%).

Sodium iodide (50 grams, 0.33 mol) was added at room temperature to an N,N-dimethylformamide (100 ml) solution of compound c (35.7 grams, 50 mmol) and the mixture was stirred for 2 hours at 70° C. Water was added after cooling and the mixture was extracted three times with ethyl acetate (400 ml). The organic layer was washed with saturated salt water and dried over anhydrous sodium sulfate. The solvent was distilled off under reduced pressure, the residue was refined using silica gel column chromatography and compound d was obtained (25.6 grams, 55%).

Sodium hydride (60%) (2.64 grams, 66 mmol) was added at 0° C. slowly in such a way that the reaction temperature did not rise to a tetrahydrofuran (50 ml) solution of compound d (18.6 grams, 20 mmol) and the mixture was stirred for 15 minutes. Then 50 ml of 0.1N dilute hydrochloric acid was added at 0° C. and the mixture was extracted three times with ethyl acetate (100 ml). The organic layer was washed with water and saturated salt water and dried over anhydrous sodium sulfate. The solvent was distilled off under reduced pressure, acetonitrile (10 ml) was added to the residue and compound e (1.08 grams, 8%) was obtained on recovering the sediment by suction filtration.

Compound f (0.71 grams, 1.8 mmol) was dissolved in 5 ml of methylene chloride and sulfuryl chloride (0.29 grams, 2.2 mmol) was added slowly in a dropwise manner at room temperature and the mixture was then stirred as it was for 30 minutes. The excess sulfuryl chloride and methylene chloride were distilled off under reduced pressure and 5 ml of methylene chloride were added to the residue. This formed solution X.

Compound e (1.08 grams, 1.6 mmol) was dissolved in 5 ml of dimethylformamide and solution X was added slowly in a dropwise manner at room temperature and the mixture was stirred for 1 hour. After the reaction, 50 ml of ethyl acetate was added and the mixture was washed with water. After drying the ethyl acetate layer, it was distilled under reduced pressure and the residue was crystallized with acetonitrile and in this way the target illustrative compound 1 (1.39 grams, 81%) was obtained.

The peak absorption wavelength, the molecular extinction coefficient and the half width value in ethyl acetate solution of the dye A obtained from illustrative compound 1 were measured.

| Dye (A) |
| --- |

-continued

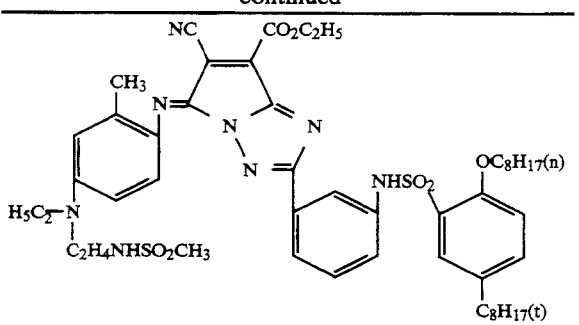

| Peak Absorption Wavelength (nm) | Molecular Extinction Coefficient | Half Width (nm) |
| --- | --- | --- |
| 629 | $5.2 \times 10^4$ | 88 |

In this way, the cyan dye obtained from a coupler of the present invention is excellent and has the peak absorption wavelength of a cyan dye. Further, it is clear that the molecular extinction coefficient of the cyan dye is high and that hue of the cyan dye has excellent sharpness.

Example of Synthesis 2

Illustrative compound 10 was prepared using the route indicated below.

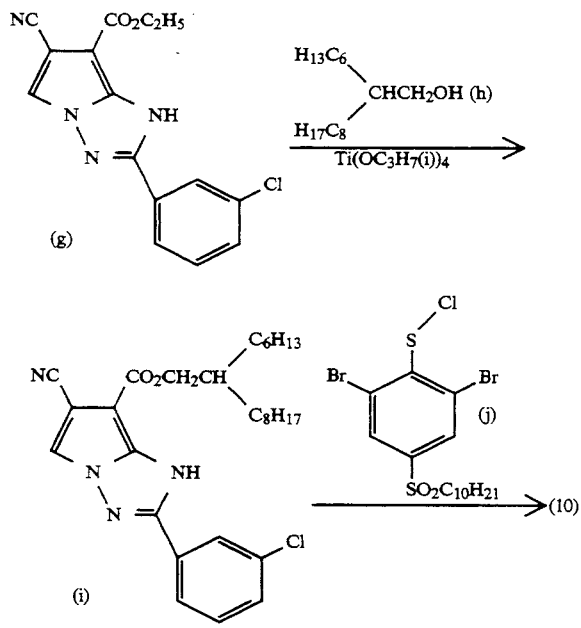

Compound g, (2.3 grams, 7.3 mmol) prepared in the same manner as in the Example of Synthesis 1, and 10 ml of compound h were dissolved in 5 ml of sulforane and then 2.1 grams of titanium isopropoxide were added. The reaction temperature was maintained at 140° C. and, after reacting for 2 hours, ethyl acetate was added. The mixture was then washed with water. After drying, the ethyl acetate layer was distilled and the residue was refined using column chromatography, whereupon compound i was obtained (3.45 grams, yield 93%).

Compound j, (2.3 grams, 4.5 mmol) prepared in the same manner as in the Example of Synthesis 1, was added to 5 ml of a dimethylformamide solution of compound i (2.0 grams, 3.9 mmol). The mixture was stirred for 1 hour at room temperature. After reaction, ethyl acetate was added and the mixture was washed with water. After drying, the ethyl acetate layer was distilled under reduced pressure. The residue was refined using column chromatography, whereupon 3.1 grams of the target illustrative compound 10 were obtained (Yield 75%).

Other compounds can be prepared using the same procedure.

The photosensitive material of the present invention should have on a support at least 1 layer which contains a coupler of the present invention. The layer which contains the coupler of the present invention should be a hydrophilic colloid layer which is on a support. General photosensitive materials can be constructed by coating layer by layer on a support, at least one blue sensitive silver halide emulsion layer, at least one green sensitive silver halide emulsion layer and at least one red sensitive silver halide emulsion layer in this order. A different order can be used. Furthermore, an infrared photosensitive silver halide emulsion layer may be used in place of at least one of the aforementioned photosensitive emulsion layers. Color reproduction with the subtractive color method can be achieved by including silver halide emulsions which are sensitized to the respective wavelength regions, and color couplers which form dyes having a complimentary color relationship with the light to which the emulsions are photosensitive, in these photosensitive emulsion layers. However, structures wherein the abovementioned correspondence between the photosensitive emulsion layer and the hue of the color which is formed by the color coupler does not hold, can also be used.

In a case where a coupler of the present invention is used in a photosensitive material, it is used as a cyan coupler, most desirably, in a red sensitive silver halide emulsion layer.

The amount of coupler of the present invention included in a photosensitive material is appropriately in the range from $1 \times 10^{-3}$ mol to 1 mol per mol of silver halide in the same layer. An amount of from $2 \times 10^{-3}$ mol to $5 \times 10^{-1}$ mol per mol of silver halide in the same layer is preferred.

The couplers of present invention can be introduced into the photosensitive material using a variety of known methods of dispersion. The oil-in-water dispersion method in which the couples are dissolved in a high boiling point organic solvent (with the conjoint use of a low boiling point organic solvent as required), emulsified, dispersed in an aqueous gelatin solution, and added to the silver halide emulsion is preferred.

Examples of the high boiling point solvents which can be used in the oil-in-water dispersion method have been disclosed, for example, in U.S. Pat. No. 2,322,027. Furthermore, as a polymer dispersion method, the processes and effects of the latex dispersion method and actual examples of latexes for loading purposes have been disclosed, for example, in U.S. Pat. No. 4,199,363, West German Patent Applications (OLS) 2,541,274 and 2,541,230, JP-B-53-41091 and European Patent laid open 029104A. Dispersion with organic solvent soluble polymers has been disclosed in PCT International Patent Laid Open No. WO88/00723. (The term "JP-B" as used herein signifies an "examined Japanese patent document".)

Examples of high boiling point solvents which can be used in the oil-in-water dispersion method include phthalic acid esters (for example, dibutyl phthalate, dioctyl phthalate, dicyclohexyl phthalate, di-2-ethylhexyl phthalate, decyl phthalate, bis(2,4-di-tert-amylphenyl)isophthalate and bis(1,1-diethylpropyl)phthalate), phosphoric acid or phosphonic acid esters (for example, diphenyl phosphate, triphenyl phosphate, tricresyl phosphate, 2-ethylhexyl diphenyl phosphate, dioctyl butyl phosphate, tricyclohexyl phosphate, tri-2-ethylhexyl phosphate, tridodecyl phosphate and di-2-ethylhexyl phenyl phosphate), benzoic acid esters (for example 2-ethylhexyl benzoate, 2-ethylhexyl-2,4-dichlorobenzoate), dodecyl benzoate, 2-ethylhexyl p-hydroxybenzoate), amides (for example, N,N-diethyldodecanamide and N,N-diethyllaurylamide), alcohols (for example, iso-stearyl alcohol), aliphatic esters (for example, dibutoxyethyl succinate, di-2ethylhexyl succinate, 2-hexyldecyl tetradecanoate, tributyl citrate, diethyl azelate, iso-stearyl lactate and trioctyl citrate), aniline derivatives (for example, N,N-dibutyl-2-butoxy-5-tert-octylaniline), chlorinated paraffins (for example paraffins which have a chlorine content of 10% to 80%), esters of trimesic acid (for example, tributyl trimesate), dodecylbenzene, diisopropylnaphthalene, phenols (for example, 2,4-di-tertamylphenol, 4-dodecyloxyphenol, 4-dodecyloxycarbonylphenol and 4-(4-dodecyloxyphenylsulfonyl) phenol), carboxylic acids (for example, 2-2,4-di-tertamylphenoxybutyric) acid and 2-ethoxyoctanedecanoic acid), and alkyl or aryl phosphoric acids (for example, di-2(ethylhexyl) phosphoric acid, and diphenyl phosphoric acid). From among these, the phosphoric acid or phosphonic acid esters and aliphatic esters are preferred.

Furthermore, organic solvents which have a boiling point above 30° C. and below about 160° C. (for example ethyl acetate, butyl acetate, ethyl propionate, methyl ethyl ketone, cyclohexanone, 2-ethoxyethyl acetate and dimethylformamide) can be used conjointly as auxiliary solvents.

The high boiling point organic solvents can be used in amounts of from 0 to 10.0 times, preferably from 0 to 6.0 times, and most desirably from 2.0 to 4.0 times, the amount of coupler in terms of the ratio by weight.

The use of the silver halide emulsions and other elements (additives etc.) which are suitable for use in the photosensitive material of the present invention, the photographic layer structures (layer arrangements etc.), the methods of processing which are suitable for processing these photosensitive materials and the additives for processing purposes which have been disclosed in the patents indicated below, and especially in European Patent EP0,355,660A2, are desirable.

| Photographic Structural Element | JP-A-62-215272 | JP-A-2-33144 | EP0,355,660A2 |
|---|---|---|---|
| Silver Halide Emulsions | Upper right column on page 10, line 6, to lower left column on page 12, line 5, and lower right column on page 12, fourth line from the bottom, to upper left column on page 13, line 17. | Upper right column on page 28, line 16, to lower right column on page 29, line 11, and page 30, lines 2 to 5. | Page 45 line 53 to page 47 line 3, and page 47 lines 20 to 22 |
| Silver Halide Solvents | Lower left column on page 12, lines 6 to 14, and upper left column on page 13, line 3 from the bottom, to lower left column on page 18, last line | — | — |
| Chemical Sensitizers | Page 12, lower left column, line 3 from the bottom, to lower right column line 5 from the bottom and lower right column on page 18, line 1, to upper right column on page 22, line 9 from the bottom | Lower right column on page 29 line 12 to the last line. | Page 47, lines 4 to 9 |
| Spectral Sensitizers (Methods of Spectral Sensitization) | Upper right column on page 22, line 8 from the bottom, to last line on page 38 | Upper left column on page 30, lines 1 to 13. | Page 47, lines 10 to 15 |
| Emulsion Stabilizers | Upper left column on page 39, line 1, to upper right column on page 72, last line | Upper left column on page 30, line 14, to upper right column line 1 | Page 47, lines 16 to 19 |
| Development Accelerators | Lower left column on page 72, line 1, to upper right column on page 91, line 3 | — | — |
| Color Couplers (Cyan, Magenta and Yellow Couplers) | Upper right column on page 91, line 4, to upper left column on page 121, line 6 | Upper right column on page 3, line 14, to upper left column on page 18, last line, and upper right column on page 30, line 6, to lower right column on page 35, line 11 | Page 4, lines 15 to 27, page 5 line 30 to the last line on page 28, page 45 lines 29 to 31 and page 47, line 23, to page 63, line 50 |
| Color Intensifiers | Upper left column on page 121, line 7, to upper right column opage 125, line 1 | — | — |
| Ultraviolet Absorbers | Upper right column on page 125, line 2, to lower left column on page 127, last | Lower right column on page 37, line 14, to upper left column on page 38, line 11 | Page 62, lines 22 to 31 |

| Photographic Structural Element | JP-A-62-215272 | JP-A-2-33144 | EP0,355,660A2 |
|---|---|---|---|
| | line | | |
| Anti-fading Agents (Image Stabilizers) | Lower right column on page 127, line 1, to lower left column on page 137, line 8 | Upper right column on page 36, line 12, to upper left column on page 37, line 19 | Page 4, line 30 to page 5, line 23, page 29, line 1 to page 45, line 25, page 45, lines 33 to 40, page 65, lines 2 to 21 |
| High Boiling Point and/or Low Boiling Point Organic Solvents | Lower left column on page 137, line 9, to upper right column on page 144, last line | Lower right column on page 35, line 14, to upper left column on page 36, line 4 from the bottom | Page 64, lines 1 to 51 |
| Methods for the Dispersion of Photographically Useful Additives | Lower left column on page 144, line 1, to upper right column on page 146, line 7 | Lower right column on page 27, line 10, to upper left column on page 28, last line, and lower right column on page 35, line 12, to upper right column, page 36, line 7 | Page 63, line 51 to page 64, line 56 |
| Film Hardening Agents | Upper right column on page 146 line 8, to lower left column on page 155, line 4 | — | — |
| Developing Agent Precursors | Lower left column on page 155, line 5, to lower right column on page 155, line 2 | — | — |
| Development Inhibitor Releasing Compounds | Lower right column on page 155, lines 3 to 9 | — | — |
| Supports | Lower right column on page 155, line 19, to upper left column on page 156, line 14 | Upper right column on page 38, line 18, to upper left column on page 39, line 3 | Page 66, line 29 to page 67, line 13 |
| Sensitive Material Layer Structure | Upper left column on page 156, line 15, to lower right column on page 156, line 14 | Upper right column on page 28, lines 1 to 15 | Page 45, lines 41 to 52 |
| Dyes | Lower right column on page 156, line 15, to lower right column on page 184, last line | Upper left column on page 38, line 12, to upper right column, line 7 | Page 66, lines 18 to 22 |
| Anti-color Mixing Agents | Upper left column on page 185, line 1, to lower right column on page 188, line 3 | Upper right column on page 36, lines 8 to 11 | Page 64, line 57 to page 65, line 1 |
| Gradation Control Agents | Lower right column on page 188, lines 4 to 8 | — | — |
| Anti-staining Agents | Lower right column on page 188, line 9, to lower right column on right column, page 193, line 10 | Upper left column on page 37, last line, to lower line 13 | Page 65, line 32 to page 66, line 17 |
| Surfactants | Lower left column on page 201, line 1, to upper right column on right column on page 210, last line | Upper right column on page 18, line 1, to lower page 24, last line, and lower left column on page 27, line 10 from the bottom, to lower right column, line 9 | — |
| Fluorine Containing Compounds (Anti-static agents, coating promotors, lubricants, anti-stick agents and the like) | Lower left column on page 210, line 1, to lower left column on page 222, line 5 | Upper left column on page 25, line 1, to lower right column on page 27, line 9 | — |
| Binders Hydrophilic colloids) | Lower left column on page 222, line 6, to upper left column on page 225, last line | Upper right column on page 38, lines 8 to 18 | Page 66, lines 23 to 28 |
| Thickeners | Upper right column on page 225, line 1, to upper right column on page 227, line 2 | — | — |
| Anti-static Agents | Upper right column on page 227, line 3, to upper left column on page 230, line 1 | — | — |
| Polymer Latexes | Upper left column on page 230, line 2, to page 239, last line | — | — |
| Matting Agents | Upper left column on page 240, line 1, to upper right | — | — |

| Photographic Structural Element | JP-A-62-215272 | JP-A-2-33144 | EP0,355,660A2 |
|---|---|---|---|
| Photographic Processing Methods (Processing operations and additives etc.) | column on page 240, last line Upper right column on page 3, line 7, to upper right column on page 10, line 5 | Upper left column on page 39, line 4, to upper left column on page 42, last line | Page 67, line 14, to page 69, line 28 |

NOTES
The citations from JP-A-62-215272 also include the details amended in accordance with the procedural amendment dated 16th March 1987 which is appended to the end of the specification.
Furthermore, from among the color couplers mentioned above, the use of the so-called short wave-type yellow couplers disclosed in JP-A-63-231451, JP-A-63-123047, JP-A-63-241547, JP-A-1-173499, JP-A-1-213648 and JP-A-1-250944, the cycloalkane type acetanilide yellow couplers disclosed in JP-A-4-116643 and the indolinocarbonylanilide based yellow couplers disclosed in European Patent Laid Open 0,482,552 as yellow couplers are preferred.

Silver chloride, silver bromide, silver chlorobromide, silver iodochlorobromide, silver iodochloride, or silver iodobromide, for example, can be used for the silver halide which is used in the present invention: However, the use of an essentially silver iodide-free silver chlorobromide of which the silver chloride content is at least 90 mol. %, preferably at least 95 mol. % and most desirably at least 98 mol. %, or a pure silver chloride emulsion, is particularly desirable for the purposes of rapid processing.

The dyes (and from among them the oxonol dyes) which can be decolorized by processing disclosed on pages 27 to 76 of European Patent EP0,337,490A2 are sometimes added to the hydrophilic colloid layer in the photosensitive material of the present invention, in such a way that the optical reflection density at 680 nm of the photosensitive material is at least 0.70 with a view to improving the sharpness of the image. Also, it is desirable to have at least 12 percent by weight (and preferably at least 14 percent by weight) of titanium oxide which has been surface treated with a di-hydric—tetrahydric alcohol (for example trimethylol-ethane) in the water resistant resin layer of the support.

Furthermore, compounds which improve the storage properties of the colored image as disclosed in European Patent EP 0,277,589A2 are preferably used with the present couplers in the photosensitive material of the present invention. Their conjoint use with pyrazoloazole-based magenta couplers is especially desirable.

That is to say, the use of compounds which improve storage properties either simultaneously or independently of compounds F which bond chemically with aromatic amine-based developing agents which remain after color development processing to form compounds which are chemically inert and essentially colorless and/or compounds G which bond chemically with the oxidized form of aromatic amine-based color developing agents which remain after color development processing and form chemically inert, essentially colorless compounds, is desirable. The use or storage after processing of the compounds which improve storage stability prevents the occurrence of staining due to the formation of colored dyes by the reaction of couplers with a color developing agent or due to the oxidized form of a color developing agent remaining in the film, or prevent other side effects.

Furthermore, the addition of biocides (such as those disclosed in JP-A-63-271247) to the photosensitive material of the present invention is desirable for preventing the growth of various fungi and bacteria which propagate in the hydrophilic colloid layers and cause deterioration of the image.

Furthermore, white polyester-based supports for display purposes or supports which have a layer containing a white pigment on the side of the support on which the silver halide emulsion layer is to be established, may be used as the support for the photosensitive material of the present invention. Moreover, the coating of an anti-halation layer on the side of the support on which the silver halide emulsion layer is coated or on the reverse side, is desirable for improving sharpness. It is especially desirable to establish a support transmission density within the range of 0.35 to 0.8 so that the display can be viewed using both reflected light and transmitted light.

The photosensitive material made in accordance with the present invention may be exposed using visible light or it may be exposed using infrared light. Low brightness exposures or high brightness short time exposures may be used for the method of exposure. In the latter case, a laser scanning exposure system wherein the exposure time per picture element is shorter than $10^{-4}$ second is preferred.

Furthermore, use of the band stop filters disclosed in U.S. Pat. No. 4,880,726 is desirable when making an exposure. Mixed color light is removed by these filters and color reproduction is markedly improved.

Formaldehyde is generally used as a stabilizing agent in a stabilizer for use with color negative films. Formaldehyde can be used as a stabilizing agent in the present invention. However, from the viewpoints of operational and environmental safety, the use of N-methylolpyrazole, hexamethylenetetramine, formaldehyde/bisulfite adducts, dimethylolurea and triazole derivatives (such as 1,4-bis(1,2,4-triazol-1-ylmethyl)piperazine) is preferred. From among these, it is desirable to conjointly use (EP 519190A) a triazole such as 1,2,4-triazole and derivatives such as 1,4-bis(1,2,4-triazol-1-ylmethyl)piperazine, and N-methylolpyrazole obtained by reacting formaldehyde and pyrazole, which provide for high image stability and low formaldehyde vapor pressure.

The invention is described below by means of illustrative examples, but the invention is not limited by these examples.

EXAMPLE 1

Preparation of Sample 101

Sample 101 of which the layer structure is indicated below was prepared on a cellulose triacetate film base.

The first layer coating liquid was prepared in the way described below.

Preparation of the First Layer Coating Liquid

The cyan coupler (ExC-1) (1.0 gram) and 4.0 grams of tricresyl phosphate were completely dissolved with the addition of 10.0 cc of ethyl acetate. This ethyl acetate solution of the coupler was added to 42 grams of 10% aqueous gelatin solution (which contained 5 grams/liter of sodium dodecylbenzenesulfonate) and emulsification and dispersion were carried out in a homogenizer. After emulsification and dispersion, distilled water was added to make a total weight of 100 grams. A solution was formed by mixing a red sensitive high silver chloride emulsion (silver bromide content 0.6 mol. %, to which $1.1 \times 10^{-4}$ mol per mol of silver halide of the red sensitive sensitizing dye indicated below had been added) with this 100 grams of emulsified dispersion to prepare the first layer coating liquid of which the composition was as indicated below.

1-Oxo-3,5-dichloro-s-triazine sodium salt was used as a gelatin film hardening agent.

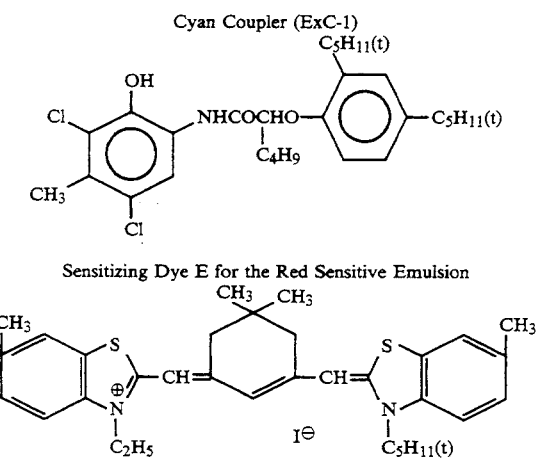

Cyan Coupler (ExC-1)

Sensitizing Dye E for the Red Sensitive Emulsion

Layer Structure

The structure of each layer was as indicated below.

Support Cellulose triacetate film

| First Layer (Emulsion Layer) | |
|---|---|
| Red sensitive high silver chloride emulsion calculated as silver | 0.42 g/m² |
| Gelatin | 1.80 g/m² |
| Cyan coupler (ExC-1) | 0.30 g/m² |
| Tricresyl phosphate | 1.20 g/m² |
| Second Layer (Protective Layer) | |
| Gelatin | 1.60 g/m² |

Preparation of Samples 102 to 111

These were prepared in the same way as sample 101 except that the couplers shown in Table A were used in an amount equimolar with the cyan coupler (ExC-1) to replace the cyan coupler (ExC-1) in sample 101.

Samples 101 to 111 which had been prepared in this way were evaluated in the ways indicated below.

Evaluation A: Color Forming properties

Each sample which had been stored for 2 days at 25° C. and 55% RH, was subjected to a white light exposure through a continuous wedge for sensitometric purposes using a sensitometer (FWH model, made by the Fuji Photo Film Co., Ltd., light source color temperature 3200°K). The samples were then developed and processed via the processing operations indicated below. Next, each sample was subjected to density measurements through a red filter and sensitometric curves were prepared. The maximum color forming densities ($D_{max}$) were read from these curves. The color forming properties are more desirable as the value of $D_{max}$ increases.

Evaluation B: Stability of the Coupler in a Photosensitive Material

Each sample which had been stored for 2 days under the conditions of 60° C. and 60% RH was exposed, processed and subjected to density measurements in the same way as in the aforementioned evaluation A. The maximum color forming densities ($D_{max}$) were then read. The fractional values of $D_{max}$ obtained from the samples which had been stored under the conditions of 60° C. and 60% RH with respect to the value for $D_{max}$ obtained form the samples which had been stored under the conditions of 25° C. and 55% RH were calculated as a percentage. The coupler was more stable in the photosensitive material as the numerical value obtained approached 100.

Evaluation C: Dye Image Fastness

The samples obtained in Evaluation A were stored for 7 days under the conditions of 80° C. and 70% RH in forced color fading tests and the density measurements were taken once again. The relative residual density after fading at the point of initial density 1.0 was calculated as a percentage.

The processing operations and the compositions of the processing liquids are indicated below.

| Processing Operation | Temperature | Time |
|---|---|---|
| Color development | 38° C. | 30 seconds |
| Bleach-fix | 35° C. | 45 seconds |
| Rinse (1) | 35° C. | 30 seconds |
| Rinse (2) | 35° C. | 30 seconds |
| Rinse (3) | 35° C. | 30 seconds |
| Drying | 80° C. | 60 seconds |

(A counter-flow system from rinse (3) → rinse (1) was used.)

The composition of each processing liquid was as indicated below.

| Color Developer | |
|---|---|
| Water | 800 ml |
| Ethylenediamine-N,N,N',N'-tetra-methylenephosphonic acid | 3.0 grams |
| Triethanolamine | 8.0 grams |
| Potassium chloride | 3.1 grams |
| Potassium bromide | 0.015 grams |
| Potassium carbonate | 25 grams |
| Hydrazino di-acetic acid | 5.0 grams |
| N-Ethyl-N-(β-methanesulfonylamido-ethyl)-3-methyl-4-aminoaniline sulfate | 5.0 grams |
| Fluorescent whitener (WHITEX-4, made by Sumitomo Chemicals) | 2.0 grams |
| Water to make a total volume of | 1000 ml |
| pH (adjusted with potassium hydroxide) | 10.05 |
| Bleach-fixer | |
| Water | 400 ml |
| Ammonium thiosulfate solution (700 g/l) | 100 ml |
| Ammonium sulfite | 45 grams |
| Ethylenediamine tetra-acetic acid | 55 grams |

-continued

| | |
|---|---|
| iron(III) ammonium salt | |
| Ethylenediamine tetra-acetic acid | 3 grams |
| Ammonium bromide | 30 grams |
| Nitric acid (67%) | 27 grams |
| Water to make up to | 1000 ml |
| pH | 5.8 |

Rinse Liquid

Ion exchanged water
(Calcium and magnesium both 3 ppm or less)

TABLE A

| Sample No. | Type of Coupler | $D_{max}$ | Coupler Stability (%) | Fastness (%) | Remarks |
|---|---|---|---|---|---|
| 101 | ExC-1 | 1.16 | 90 | 50 | For Comparison |
| 102 | ExC-2 | 1.20 | 85 | 68 | " |
| 103 | ExC-3 | 1.90 | 40 | 60 | " |
| 104 | ExC-4 | 1.10 | 90 | 60 | " |
| 105 | (1) | 2.02 | 91 | 92 | This Invention |
| 106 | (4) | 2.00 | 91 | 92 | " |
| 107 | (9) | 2.06 | 90 | 93 | " |
| 108 | (10) | 2.08 | 92 | 92 | " |
| 109 | (12) | 2.01 | 93 | 95 | " |
| 110 | (16) | 2.06 | 95 | 92 | " |
| 111 | (23) | 1.95 | 82 | 90 | " |

The couplers for comparison, (ExC-2), (EXC-3) and (ExC-4), are indicated below.

Comparative Coupler (ExC-2)

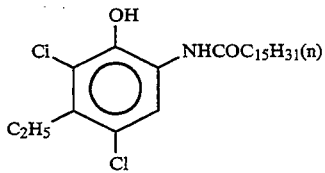

Comparative Coupler (ExC-3) Disclosed in European Patent Laid Open 0456226

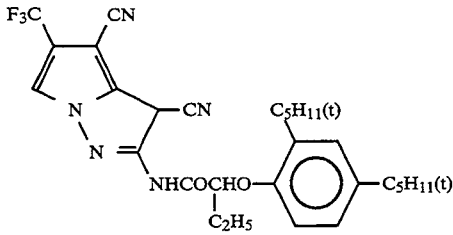

Comparative Coupler (ExC-4) Disclosed in European Patent Laid Open 0484909

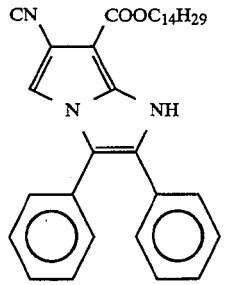

It can be concluded from Table A that with the samples using couplers outside the scope of the present invention, the performance with respect to the three factors of color formation, coupler stability and image fastness were not satisfied. Further, the samples using couplers of the present invention were excellent in all of these aspects of performance.

Furthermore, with the samples using couplers of the present invention, it was observed visually that the color of the dye image obtained after processing was brilliant and highly transparent. Further, it was confirmed by measuring the spectral absorption spectra that there was little absorbance in the yellow or magenta regions and the dye image had an excellent hue.

EXAMPLE 2

A multi-layer color printing paper (sample 201) of which the layer structure is indicated below, was prepared by establishing a gelatin under-layer containing sodium dodecylbenzene sulfonate on the surface of a paper support previously laminated on both sides with polyethylene, following with a corona discharge treatment, and then coating the various photographic structural layers. The coating liquids were prepared in the manner indicated below.

Preparation of the Fifth Layer Coating Liquid

Ethyl acetate (60.0 cc) was added to 20.0 grams of cyan coupler (ExC), 2.0 grams of ultraviolet absorber (UV-2), 10.0 grams of colored image stabilizer (Cpd-1), 5.0 grams of colored image stabilizer (Cpd-3), 10.0 grams of colored image stabilizer (Cpd-5), 2.0 grams of colored image stabilizer (Cpd-6), 10.0 grams of colored image stabilizer (Cpd-8), 40.0 grams of solvent (Solv-3) and 20.0 grams of solvent (Solv-5), to form a solution. This solution was then added to 500 cc of a 20% aqueous gelatin solution containing 8 grams of sodium dodecylbenzenesulfonate, the resulting solution has emulsified and dispersed in an ultrasonic homogenizer to prepare emulsified dispersion C. On the other hand, the silver chlorobromide emulsion C (a 1:4 (Ag mol ratio) mixture of a cubic large grain emulsion of average grain size 0.50 μm and a cubic small grain emulsion of average grain size 0.41 μm; the variation coefficients of the grain size distributions being 0.09 and 0.11, and each emulsion having 0.8 mol. % silver bromide included locally on parts of the surface of the grains) was prepared. The red sensitive sensitizing dye E was added to the emulsion C in an amount of $0.9 \times 10^{-4}$ mol and $1.1 \times 10^{-4}$ mol per mol of silver for the emulsion which had large grains and the emulsion which had small grains, respectively. Moreover, compound F was added in an amount of $2.6 \times 10^{-3}$ mol per mol of silver halide. Furthermore, the emulsion C was chemically ripened with the addition of a sulfur sensitizer and a gold sensitizer. This red sensitive silver chlorobromide emulsion C was mixed with the aforementioned emulsified dispersion C to prepare the fifth layer coating liquid of which the composition is indicated below.

The coating liquids for the first to the fourth layers and the sixth and seventh layers were prepared using the same procedure as for the fifth layer coating liquid. 1-Oxy-3,5-dichloro-s-triazine sodium salt was used as a gelatin hardening agent in each layer.

Furthermore, Cpd-14 and Cpd-15 were added to each layer in such a way that the total amounts were 25.0 mg/m² and 50.0 mg/m² respectively.

The spectrally sensitizing dyes used in the silver chlorobromide emulsions of each photosensitive layer are indicated below.

Sensitizing Dye A

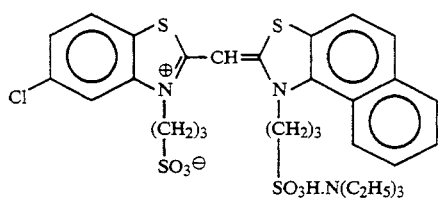

Blue Sensitizing Dye B

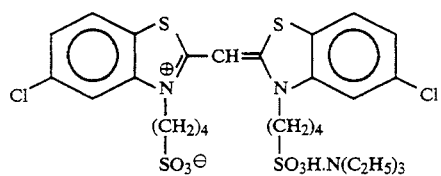

Green Sensitive Layer

Sensitizing Dye C

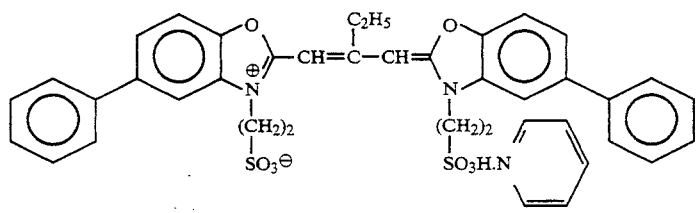

(4.0 × $10^{-4}$ mol per mol of silver halide for the large size emulsion B and 5.6 × $10^{-4}$ mol per mol of silver halide for the small size emulsion B)

Sensitizing Dye D

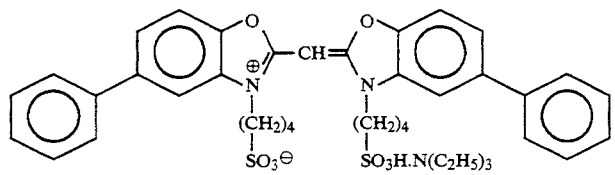

(7.0 × $10^{-5}$ mol per mol of silver halide for the large size emulsion B and 10.0 × $10^{-5}$ mol per mol of silver halide for the small size emulsion B)

Red Sensitive Layer

Sensitizing Dye E

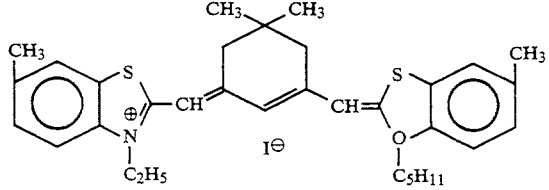

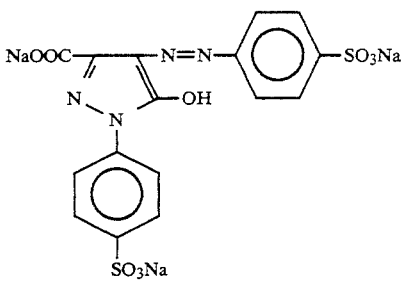

(10 mg/m²)

Compound F

[structure shown]

Furthermore, 1-(5-methylureidophenyl)-5-mercaptotetrazole was added to the blue, green and red sensitive emulsion layers in amounts, per mol of silver halide, of 8.5×$10^{-5}$ mol, 7.7×$10^{-4}$ mol and 2.5×$10^{-4}$ mol, respectively.

Furthermore, 4-hydroxy-6-methyl-1,3,3a,7-tetraazaindene was added to the blue and green sensitive emulsion layers in amounts, per mol of silver halide, of 1×$10^{-4}$ mol and 2×$10^{-4}$ mol, respectively.

The dyes indicated below (coated weights in brackets) were added to the emulsion layers for anti-irradiation purposes.

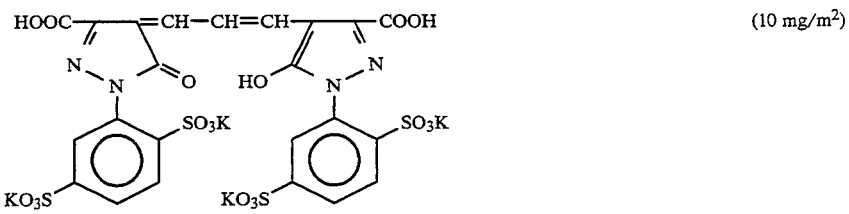

(10 mg/m²)

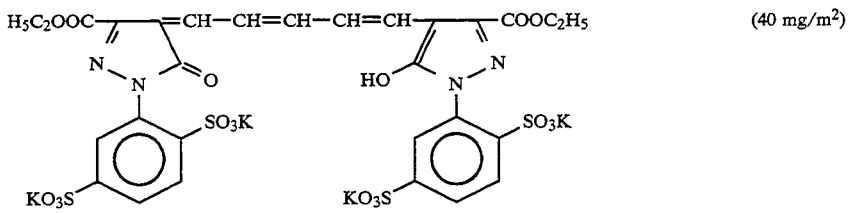

(40 mg/m²)

and

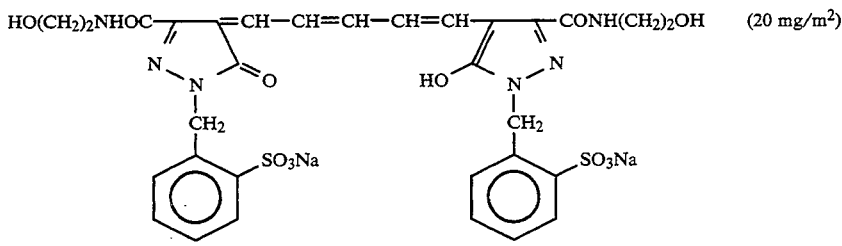

(20 mg/m²)

Layer Structure

The composition of each layer is indicated below. The numerical values indicate coated weights (g/m²). In the case of silver halide emulsions the coated weight is shown as the calculated coated weight of silver.

| | |
|---|---:|
| Support | |
| Polyethylene laminated paper | |
| [White pigment (TiO₂) and blue dye (ultramarine) were included in the polyethylene on the first layer side] | |
| First Layer (Blue Sensitive Emulsion Layer) | |
| Silver chlorobromide emulsion (a 3:7 mixture (silver mol ratio) of a cubic large grain emulsion A of average grain size 0.88 μm and a cubic small grain size emulsion A of average grain size 0.70 μm; the variation coefficients of the grain size distributions were 0.08 and 0.10 respectively, and the emulsions of each size had 0.3 mol % AgBr included locally on part of the grain surface.) | 0.27 |
| Gelatin | 1.36 |
| Yellow coupler (ExY) | 0.60 |
| Colored image stabilizer (Cpd-1) | 0.06 |
| Colored image stabilizer (Cpd-2) | 0.03 |
| Colored image stabilized (Cpd-3) | 0.06 |
| Solvent (Solv-1) | 0.10 |
| Solvent (Solv-2) | 0.10 |
| Second Layer (Anti-color Mixing Layer) | |
| Gelatin | 1.00 |
| Anti-color mixing agent (Cpd-4) | 0.07 |
| Solvent (Solv-7) | 0.03 |
| Solvent (Solv-2) | 0.25 |
| Solvent (Solv-3) | 0.25 |
| Third Layer (Green Sensitive Emulsion Layer) | |
| Silver chlorobromide emulsion (a 1:3 (silver mol ratio) mixture of a large grain cubic emulsion of average grain size 0.55 μm and a small grain emulsion of average grain size 0.39 μm; the variation coefficients of the grain size distributions were 0.10 and 0.08, respectively, and each emulsion had 0.8 mol % AgBr included locally on part of the grain surface) | 0.13 |
| Gelatin | 1.45 |
| Magenta coupler (ExM) | 0.16 |
| Colored image stabilizer (Cpd-5) | 0.15 |
| Colored image stabilizer (Cpd-2) | 0.03 |
| Colored image stabilizer (Cpd-6) | 0.01 |
| Colored image stabilizer (Cpd-7) | 0.01 |
| Colored image stabilizer (Cpd-8) | 0.08 |
| Solvent (Solv-3) | 0.50 |
| Solvent (Solv-4) | 0.15 |
| Solvent (Solv-5) | 0.15 |
| Fourth Layer (Anti-color Mixing Layer) | |
| Gelatin | 0.70 |
| Anti-color mixing agent (Cpd-4) | 0.05 |
| Solvent (Solv-7) | 0.02 |
| Solvent (Solv-2) | 0.18 |
| Solvent (Solv-3) | 0.18 |
| Fifth Layer (Red Sensitive Emulsion Layer) | |
| The aforementioned silver chlorobromide emulsion C | 0.14 |
| Gelatin | 1.10 |
| Cyan coupler (ExC) | 0.20 |
| Ultraviolet absorber (UV-2) | 0.02 |
| Colored image stabilizer (Cpd-1) | 0.10 |
| Colored image stabilizer (Cpd-3) | 0.05 |
| Colored image stabilizer (Cpd-5) | 0.10 |
| Colored image stabilizer (Cpd-6) | 0.02 |
| Colored image stabilizer (Cpd-8) | 0.10 |
| Solvent (Solv-3) | 0.40 |
| Solvent (Solv-5) | 0.20 |
| Sixth Layer (Ultraviolet Absorbing Layer) | |
| Gelatin | 0.55 |
| Ultraviolet absorber (UV-1) | 0.40 |
| Colored image stabilizer (Cpd-12) | 0.15 |
| Colored image stabilizer (Cpd-5) | 0.02 |
| Seventh Layer (Protective Layer) | |
| Gelatin | 1.13 |
| Acrylic modified poly(vinyl alcohol) (17% modification) | 0.05 |

| | |
|---|---|
| Liquid paraffin | 0.02 |
| Colored image stabilizer (Cpd-5) | 0.01 |

(ExY) Yellow Coupler

A 1:1 mixture (mol ratio) of:

[Structure: yellow coupler with pivaloyl group, CH-R, CONH-phenyl with X substituent, and NHCOCHO-phenyl with two C₅H₁₁(t) groups and C₂H₅]

where R = [benzyl-N-hydantoin with OC₂H₅], X = Cl and

R = [oxazolidinedione with CH₃, CH₃], X = OCH₃

(ExM) Magenta Coupler

[Structure: pyrazolotriazole magenta coupler with Cl, CH₃, CHCH₂NHCOCHO-phenyl(C₅H₁₁(t))₂, C₆H₁₃(n), CH₃]

(ExC) Cyan Coupler

A 7:3 mixture (mol ratio) of:

[Structure: phenol cyan coupler with Cl, OH, CH₃, Cl substituents, NHCOCHO-phenyl(C₅H₁₁(t))₂, C₄H₉]

and

[Structure: phenol with Cl, OH, NHCOC₁₅H₃₁, C₂H₅, Cl]

(Cpd-1) Colored Image Stabilizer $-(CH_2-CH)_n-$
       |
       CONHC₄H₉(t)

(Average Molecular Weight 60,000)

(Cpd-2) Colored Image Stabilizer

[Structure: bis-phenol with isopropylidene bridge, CH₃ and OH groups]

(Cpd-3) Colored Image Stabilizer

[Structure: tris(glycidyloxy-methylphenyl)methane oligomer with OCH₂CH(O)CH₂ epoxide groups, CH₃, and CH₂ bridges]

n = 7 to 8 (average value)

(Cpd-4) Anti-color Mixing Agent

[Structure: hydroquinone with two C₈H₁₇(t) groups]

(Cpd-5) Colored Image Stabilizer

[Structure: spirobiindane with OC₃H₇ groups and CH₃ substituents]

(Cpd-6)

[Structure: benzene with SO₂H, and two COOC₁₄H₂₉ / C₁₄H₂₉OC(O) ester groups]

(Cpd-7)

[Structure: benzene with SO₂Na, and two C₁₄H₂₉OC(O) ester groups]

(Cpd-8) Colored Image Stabilizer

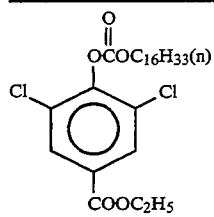
(Cpd-9) Colored Image Stabilizer
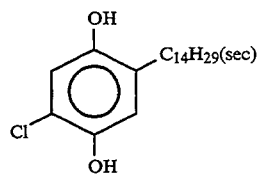
(Cpd-10) Colored Image Stabilizer
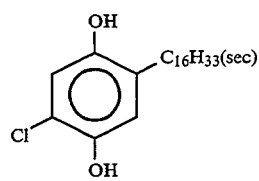
(Cpd-11)
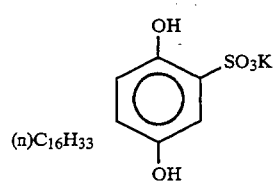
(Cpd-12)
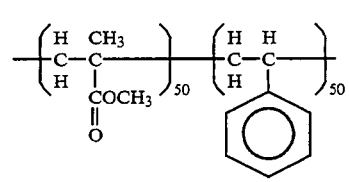
Average Molecular Weight 60,000
(Cpd-13)
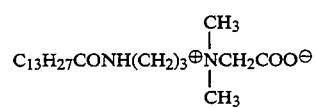
(Cpd-14) Fungicide
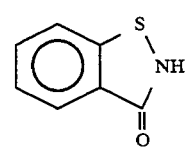
(Cpd-15) Fungicide
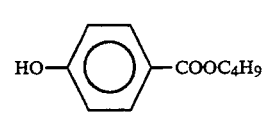
(UV-1) Ultraviolet Absorber
A 1:5:10:5 mixture (by weight) of:
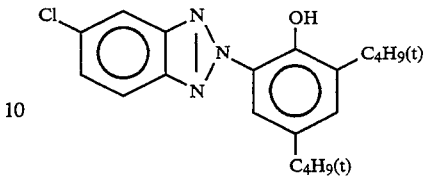
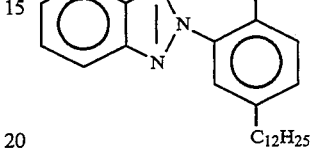
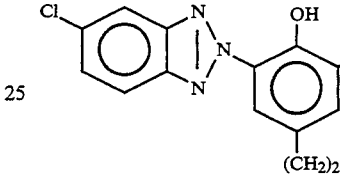
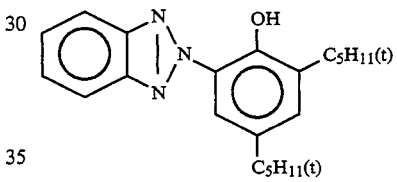
(UV-2) Ultraviolet Absorber
A 1:2:2 mixture (by weight) of:
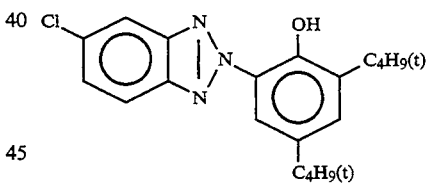
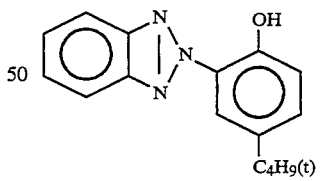
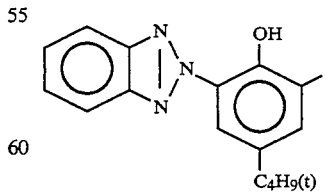
(Solv-1) Solvent
(Solv-2) Solvent -continued

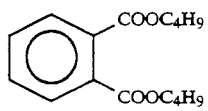

(Solv-3) Solvent

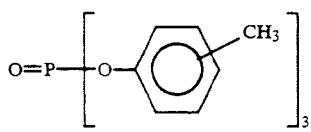

(Solv-4) Solvent

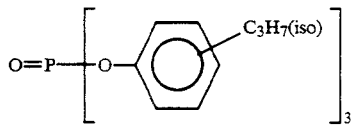

(Solv-5) Solvent

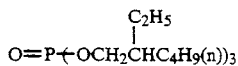

(Solv-6) Solvent

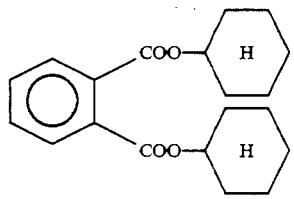

(Solv-7) Solvent

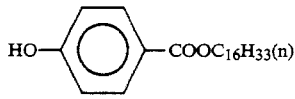

Next, samples 202 to 211 were prepared in the same way as sample 201 except that the cyan coupler (ExC) in sample 201 was replaced by equimolar amounts of the couplers indicated in Table B.

The samples 201 to 211 were subjected to a gray exposure so as to result in the development of about 30% of the coated silver using a sensitometer (FWH model, made by the Fuji Photo Film Co., Ltd., light source temperature 3200°K).

The exposed samples were subjected to continuous processing using a paper processor and the processing operations and processing liquid compositions indicated below. A development processing state of running equilibrium was attained.

| Processing Operation | Temp. | Time | Replenisher* | Tank Capacity |
|---|---|---|---|---|
| Color Development | 35° C. | 45 sec. | 161 ml | 17 liters |
| Bleach-fixing | 30–35° C. | 45 sec. | 215 ml | 17 liters |
| Rinse | 30° C. | 90 sec. | 350 ml | 10 liters |
| Drying | 70–80° C. | 60 sec. | | |

*Replenishment rate per m² of photosensitive material.

The composition of each processing liquid was as indicated below.

| Color Developer | Tank Solution | Replenisher |
|---|---|---|
| Water | 800 ml | 800 ml |
| Ethylenediamine-N,N,N',N'-tetramethylenephosphonic acid | 1.5 grams | 2.0 grams |
| Potassium bromide | 0.015 gram | — |
| Triethanolamine | 8.0 grams | 12.0 grams |
| Sodium chloride | 1.4 grams | — |
| Potassium carbonate | 25 grams | 25 grams |
| N-Ethyl-N-(β-methanesulfon-amidoethyl)-3-methyl-4-aminoaniline sulfate | 5.0 grams | 7.0 grams |
| N,N-Bis(carboxymethyl)-hydrazine | 4.0 grams | 5.0 grams |
| N,N-di(sulfoethyl)hydroxyl-amine mono-sodium salt | 4.0 grams | 5.0 grams |
| Fluorescent whitener (WHITEX 4B, made by Sumitomo Chemicals) | 1.0 gram | 2.0 grams |
| Water to make a total volume of | 1000 ml | 1000 ml |
| pH (25° C.) | 10.05 | 10.45 |

| Bleach-fix Bath (Tank Solution = Replenisher) | |
|---|---|
| Water | 400 ml |
| Ammonium thiosulfate (700 g/l) | 100 ml |
| Sodium sulfite | 17 grams |
| Ethylenediamine tetra-acetic acid, iron(III) ammonium salt | 55 grams |
| Ethylenediamine tetra-acetic acid, di-sodium salt | 5 grams |
| Ammonium bromide | 40 grams |
| Water to make up to | 1000 ml |
| pH (25° C.) | 6.0 |

Rinse Bath (Tank Solution = Replenisher)
Ion exchanged water
(Calcium and magnesium both less than 3 ppm)

Evaluation was carried out in the same way as in Example 1. The results are indicated below.

TABLE B

| Sample No. | Type of Coupler | $D_{max}$ | Coupler Stability (%) | Fastness (%) | Remarks |
|---|---|---|---|---|---|
| 201 | ExC | 1.45 | 82 | 61 | For Comparison |
| 202 | ExC-2 | 1.48 | 79 | 68 | " |
| 203 | ExC-3 | 2.20 | 51 | 60 | " |
| 204 | ExC-4 | 1.40 | 80 | 60 | " |
| 205 | (1) | 2.50 | 91 | 94 | This Invention |
| 206 | (4) | 2.50 | 91 | 92 | " |
| 207 | (9) | 2.53 | 90 | 93 | " |
| 208 | (10) | 2.52 | 92 | 92 | " |
| 209 | (12) | 2.54 | 93 | 93 | " |
| 210 | (16) | 2.53 | 95 | 94 | " |
| 211 | (23) | 2.40 | 76 | 90 | " |

The couplers for comparison, (ExC), (ExC-2), (ExC-3) and (ExC-4), are the same as those in Example 1.

According to Table B, the samples in which the coupler of the present invention had been used were assessed as having superior performance with respect to high color formation properties, coupler stability and image fastness.

Next, samples were prepared by replacing the yellow coupler (ExY) in the first layer (blue sensitive emulsion layer) of the samples of Example 2 with a equimolar amount of ExY-2 and reducing the coated silver weight of the first layer to 80%, including the coupler without changing the composition, and these samples were evaluated in the same way as in Example 1. In this case again results more or less the same as in Example 2 were obtained.

(ExY-2)
A 1:1 mixture (mol ratio) of:

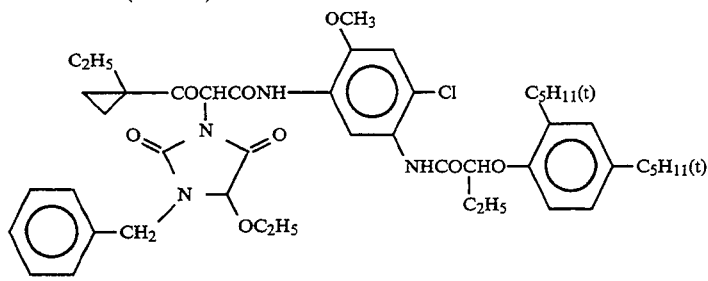

and

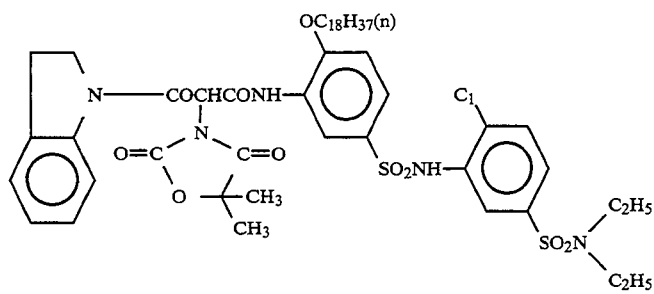

EXAMPLE 3

Sample 301 having the same structure as the photosensitive material shown as sample 110 of Example 2 disclosed in JP-A-3-154539 was prepared. Samples were prepared by replacing the cyan coupler ExC-1 in the third, fourth and fifth layers of this sample with coupler (1), (10) or (12) of the present invention. These samples were evaluated in the same way as in Example 1. The process disclosed in Example 2 of JP-A-3-154539 was used for processing samples 301 to 303. However, use was made of the stabilizer indicated below. In this case, as in Example 1 above, these results showed the superiority of the couplers of the present invention.

| Stabilizer | |
|---|---|
| Water | 900 ml |
| 1,4-Bis(1,2,4-triazol-1-ylmethyl)-piperazine | 0.3 mol |
| 1,2,4-Triazole | 2.3 mol |
| Polyoxyethylene p-mono-nonylphenyl ether (average degree of polymerization 10) | 0.3 grams |
| Ethylenediamine tetra-acetic acid, di-sodium salt | 5.5 grams |
| Sodium p-toluenesulfonate | 3.3 grams |
| Water to make a total volume of | 1000 ml |
| pH | 8.5 |

EXAMPLE 4

Sample 401 having the same structure as sample 701 of Example 7 of U.S. Pat. No. 5,122,444 was prepared. Next, samples 402 and 403 were prepared by replacing the cyan coupler (EX-2) of the third and fourth layers of Sample 401, with equimolar amounts of the couplers (1) and (10) of the present invention, and the samples were evaluated in the same way as in Example 1. In this case, as before, it was confirmed that the couplers of the present invention have superior hue, color forming properties, colored image fastness and coupler stability in the photosensitive material.

Next, a sample was prepared by adding 0.050 g/m² of EX-14 to the fourth layer, 0.020 g/m² of EX-15 to the fifth layer and 0.015 g/m² of EX-2 to the ninth layer of the abovementioned sample 403. The EX-11 and EX-13 of the ninth layer were replaced with 0.065 g/m² of EX-16 and 0.020 g/m² of EX-17, respectively. Upon evaluation in the same way as before, it was confirmed that the couplers of the present invention have excellent hue, color forming properties, colored image fastness and coupler stability in the photosensitive material.

A sample was prepared by replacing the EX-8 and EX-9 in the eleventh, twelfth and thirteenth layers with equimolar amounts of EX-18 and EX-19 respectively. Results similar to previous ones were obtained upon evaluation in the same manner as described above.

Ex-14
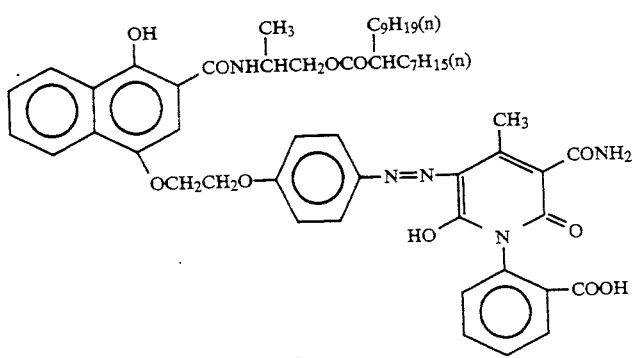
Ex-15
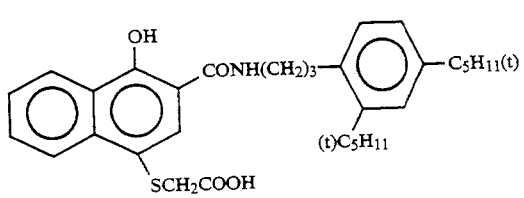
Ex-16
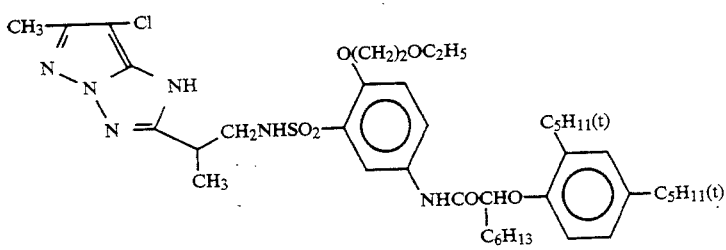
Ex-17
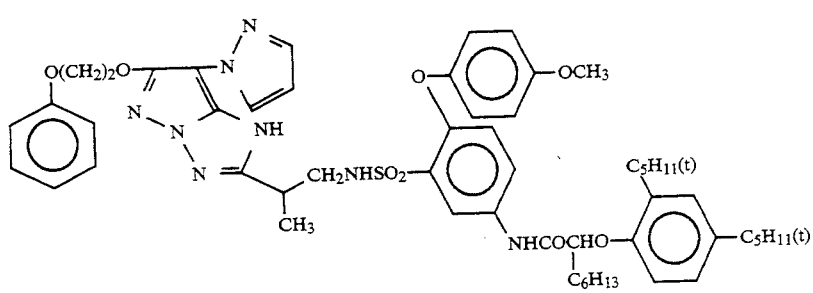
Ex-18
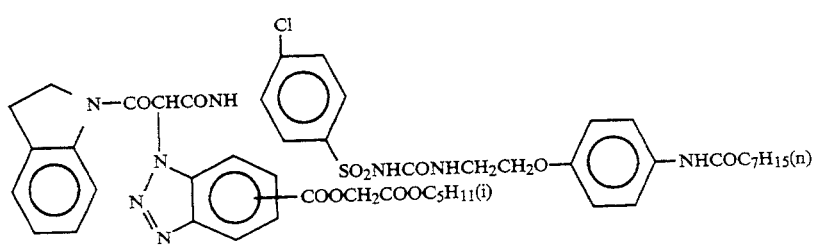
Ex-19
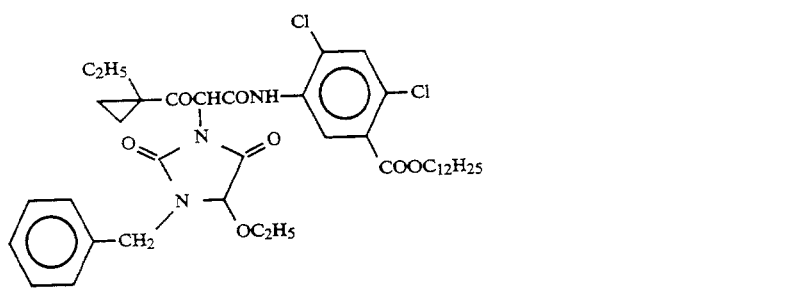

EXAMPLE 5

Sample 501 having the same structure as sample 601 of Example 6 disclosed in U.S. Pat. No. 5,122,444, was prepared. Next, samples 502 and 503 in which the cyan couplers C-1, C-2 and C-3 in the fourth, fifth and sixth layers of this sample were replaced by coupler (1) or coupler (10) of the present invention, were prepared. These samples were evaluated in the same manner as described in Example 1. Again, results showing that the couplers of the present invention are superior were obtained.

Moreover, a sample in which the C-4 and C-7 in the ninth to the eleventh layers of the abovementioned sample 503 were replaced by C-8 in an amount corresponding to 80 mol. % of the total of these compounds, and C-6 in the sixteenth and seventeenth layers was replaced with an equimolar amount of C-10, was prepared. On upon evaluation in the same manner as before, it was confirmed that these coupler samples exhibited excellent hue, color forming properties, colored image fastness and stability in the photosensitive material.

wherein Za represents —NH— or —CH($R_3$)—, and Zb and Zc each represents —C($R_4$)= or —N=; when Zb is —C($R_4$)=, Zc is not —C($R_4$)= at the same time as Za is —NH— and Zc is not —N= at the same time as Za is —CH($R_3$); $R_1$, $R_2$ and $R_3$ each represents an electron withdrawing group of which the Hammett substituent group constant $\sigma_p$ is 0.20 or above, the sum of the up values of $R_1$ and $R_2$ is 0.65 or above; $R_4$, $R_a$, $R_b$, $R_c$, $R_d$ and $R_e$ each represents a hydrogen atom or a substituent group; when there are two $R_4$ groups in formula (I) these may be the same or different; at least one of $R_a$, $R_b$, $R_c$, $R_d$ and $R_e$ represents an electron withdrawing group; and the sum of the respective Hammett substituent groups constant $\sigma_p$ values of $R_a$, $R_b$, $R_c$, $R_d$ and $R_e$ is 0.5 or above, or at least two of $R_a$, $R_b$, $R_c$, $R_d$ and $R_e$ are fluorine atoms and the sum of the respective Hammett substituent group constant $\sigma_p$ values of $R_a$, $R_b$, $R_c$, $R_d$ and $R_e$ is 0.15 or above.

2. The silver halide color photosensitive material of claim 1, wherein the $\sigma_p$ values of $R_1$, $R_2$ and $R_3$ are from 0.30 to 1.0.

3. The silver halide color photosensitive material of claim 1, wherein the sum of the values of $R_1$ and $R_2$ is

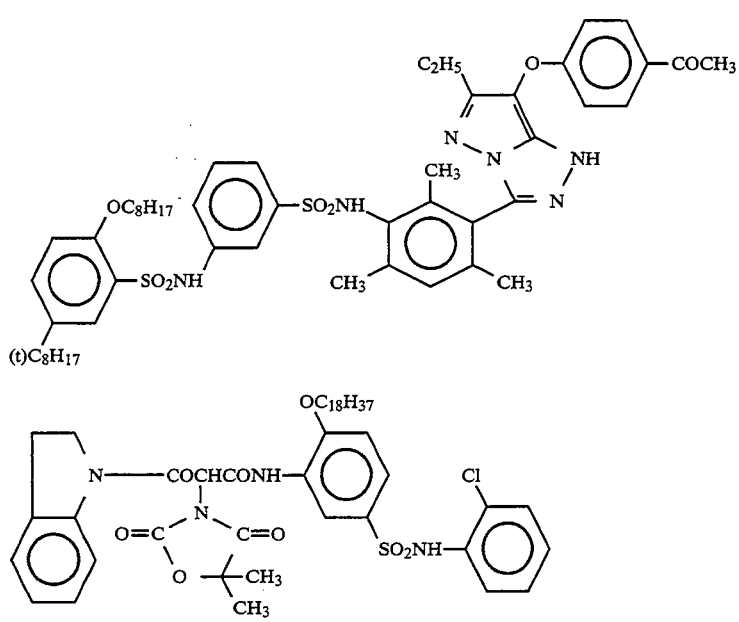

While the invention has been described in detail and with reference to specific embodiments thereof, it will be apparent to one skilled in the art that various changes and modifications can be made therein without departing from the spirit and scope thereof.

What is claimed is:

1. A silver halide color photosensitive material comprising a support having thereon a layer containing a coupler represented by formula (I) below:

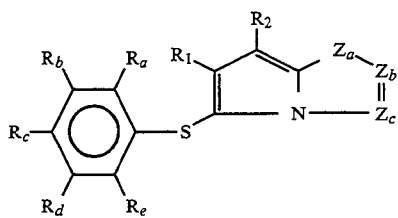

from 0.70 to 1.8.

4. The silver halide color photosensitive material of claim 1, wherein when at least one of $R_a$, $R_b$, $R_c$, $R_d$, and $R_e$ represents an electron withdrawing group, the sum of the $\sigma_p$ values of $R_a$, $R_b$, $R_c$, $R_d$ and $R_e$ is from 0.8 to 2.0.

5. The silver halide color photosensitive material of claim 1, wherein when at least one of $R_a$, $R_b$, $R_c$, $R_d$, and $R_e$ represents an electron withdrawing group, the sum of the $\sigma_p$ values of $R_a$, $R_b$, $R_c$, $R_d$ and $R_e$ is from 1.0 to 2.0.

6. The silver halide color photosensitive material of claim 1, wherein the coupler is represented by the following formula (II)

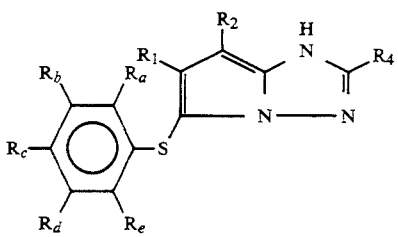

Formula (II)

wherein $R_1$, $R_2$, $R_4$, $R_a$, $R_b$, $R_c$, $R_d$ and $R_e$ are as defined in claim 1.

7. A silver halide color photosensitive material of claim 6, wherein $R^4$ in formula (II) represents a halogen atom, an alkyl group, an aryl group, a heterocyclic group, a cyano group, a hydroxy group, a nitro group, a carboxy group, a sulfo group, an amino group, an alkoxy group, an aryloxy group, an acylamino group, an alkylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocylcic oxy group, an azo group, an acyloxy group, a carbamoyloxy group, a silyloxy group, an aryloxycarbonylamino group, an imido group, a hetrocylcic thio group,, a sulfinyl group, a phosphonyl group, an aryloxycarbonyl group, an acyl group and an azolyl group.

8. A silver halide color photosensitive material of claim 6, wherein $R_4$ represents an alkyl group or an aryl group.

9. A silver halide color photosensitive material of claim 8, wherein the alkyl group or the aryl group is substituted with at least one halogen atom, a alkoxy group, a sulfonyl group, a sulfomoyl group, a carbomoyl group, an acylamido group or a sulfonamido group.

10. A silver halide color photosensitive material of claim 1, wherein the layer containing a coupler is a hydrophilic colloid layer.

11. A silver halide color photosensitive material of claim 1, wherein the coupler is a cyan coupler and the coupler is present in a red-sensitive silver halide emulsion layer.

12. A silver halide color photosensitive material of claim 1, wherein the coupler is present in an amount of $1 \times 10^{-3}$ mol to 1 mol per mol of a silver halide present in the same layer.

13. A silver halide color photosensitive material of claim 1, wherein $R1$ and $R_3$ in formula (I) each represents a cyano group.

14. A silver halide color photosensitive material of claim 1, wherein at least one of $R_a$ to $R_e$ represents an electron withdrawing group.

15. A silver halide color photosensitive material of claim 1, wherein at least two of $R_a$ to $R_e$ each represent art electron withdrawing group.

16. A silver halide color photosensitive material of claim 1, wherein each Hammet substitution constant $\sigma_p$ value of $R_a$, $R_b$, $R_c$, $Rd$, and $R_e$ is 0.2 or higher.

17. A silver halide color photosensitive material of claim 1, wherein $R_1$, $R_2$ and $R_3$ in formula (I) each represent a cyano group, an alkoxycarbonyl group or an aryloxycarbonyl group.

18. A silver halide color photosensitive material of claim 1, wherein $R^1$, $R^2$ and $R^3$ in formula (I) each represents an acyl group, an acyloxy group, a carbamoyl group, an alkoxycarbonyl group, an aryloxycarbonyl group, a cyano group, a nitro group, a dialkylphosphono group, a diarylphosphono group, a diarylphosphinyl group, an alkylsulfinyl group, an alkylsulfonyl group, an arylsulfonyl group, a sulfonyloxy group, an arylthio group, a sulfamyl group, a thiocyanato group, a thiocarbonyl group, an alkyl group which is substituted with at least two halogen atoms, an alkoxy group which is substituted with at least two halogen atoms, an aryloxy group which is substituted with at least two halogen atoms, an alkylthio group which is substituted with at least two halogen atoms, a heterocyclic group, a chlorine atom, a bromine atom, an azo group, or a selenocyanato group.

19. A silver halide color photosensitive material of claim 18, wherein $R_2$ represents a branched chain alkoxycarbonyl group.

20. A silver halide color photosensitive material of claim 1, wherein $R^1$, $R^2$ and $R^3$ in formula (I) each represents an acyl group, an alkoxycarbonyl group, a nitro group, a cyano group, an arylsulfonyl group, a carbamoyl group or an alkyl group which is substituted with two or more halogen atoms.

21. A silver halide color photosensitive material of claim 1, wherein the substituent group defined in $R^a$, $R^b$, $R^c$, $R^d$ and $R^e$ of formula (I) each represents a halogen atom, an alkyl group, an aryl group, a heterocylcic group, a cyano group, a hydroxy group, a nitro group, a carboxy group, a sulfo group, an amino group, an alkoxy group, an aryloxy group, an acylamino group, an alkylamino group, an anilino group, a ureido group, a sulfamoylamino group, an alkylthio group, an arylthio group, an alkoxycarbonylamino group, a sulfoamido group, a carbamoyl group, a sulfamoyl group, a sulfonyl group, an alkoxycarbonyl group, a heterocylic group, an azo group, an acyloxy group, a carbamoyloxy group, a silyoxy group, an aryloxycarbonylamino group, an imido group, a heterocyclic thio group, a sulfinyl group, a phosphonyl group, an aryloxycarbonyl group, an acyl group or an azoyl group.

22. A silver halide color photosensitive material of claim 1, wherein the electron withdrawing groups for $R^a$ to $R^e$ in formula (I) each is a bromine atom, a chlorine atom, a carbamoyl group, an alkoxycarbonyl group, a cyano group, a nitro group, an alkylsulfinyl group, an arylsulfinyl group, an alkylsulfonyl group, an arylsulfonyl group, a sulfonyloxy group, a sulfamoyl group or a haloalkyl group.

* * * * *